US011261215B2

(12) United States Patent
Hoffman et al.

(10) Patent No.: US 11,261,215 B2
(45) Date of Patent: Mar. 1, 2022

(54) SOMATOSTATIN PRODRUGS

(71) Applicant: YISSUM RESEARCH DEVELOPMENT COMPANY OF THE HEBREW UNIVERSITY OF JERUSALEM LTD., Jerusalem (IL)

(72) Inventors: Amnon Hoffman, Jerusalem (IL); Chaim Gilon, Jerusalem (IL); Adi Klinger, Rishon Lezion (IL); Johnny Naoum, Haifa (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 0 days.

(21) Appl. No.: 16/648,292

(22) PCT Filed: Sep. 17, 2018

(86) PCT No.: PCT/IL2018/051038
§ 371 (c)(1),
(2) Date: Mar. 18, 2020

(87) PCT Pub. No.: WO2019/058365
PCT Pub. Date: Mar. 28, 2019

(65) Prior Publication Data
US 2020/0262871 A1    Aug. 20, 2020

Related U.S. Application Data

(60) Provisional application No. 62/560,216, filed on Sep. 19, 2017.

(51) Int. Cl.
*A61K 38/00* (2006.01)
*C07K 7/64* (2006.01)

(52) U.S. Cl.
CPC ............... *C07K 7/64* (2013.01); *A61K 38/00* (2013.01)

(58) Field of Classification Search
CPC ...... A61K 38/00; A61K 38/31; A61K 9/0019; A61K 9/0053; C07K 14/6555; C07K 7/64
See application file for complete search history.

(56) References Cited

U.S. PATENT DOCUMENTS

| | | | |
|---|---|---|---|
| 5,770,687 A | 6/1998 | Hornik | |
| 5,811,392 A | 9/1998 | Gilon | |
| 5,874,529 A | 2/1999 | Gilon | |
| 5,883,293 A | 3/1999 | Gilon | |
| 6,051,554 A | 4/2000 | Hornik | |
| 6,117,974 A | 9/2000 | Gilon | |
| 6,265,375 B1 | 7/2001 | Gilon | |
| 6,355,613 B1 | 3/2002 | Hornik | |
| 6,407,059 B1 | 6/2002 | Gilon | |
| 6,512,092 B2 | 1/2003 | Falb | |
| 6,943,145 B2 * | 9/2005 | Bodor | A61K 47/62 514/11.1 |
| 2004/0152769 A1 | 8/2004 | Ekwuribe | |

FOREIGN PATENT DOCUMENTS

| | | |
|---|---|---|
| WO | 9533765 A1 | 12/1995 |
| WO | 9709344 A2 | 3/1997 |
| WO | 9712904 A1 | 4/1997 |
| WO | 9804583 A1 | 2/1998 |
| WO | 9912572 A1 | 3/1999 |
| WO | 9931121 A2 | 6/1999 |
| WO | 9965508 A1 | 12/1999 |
| WO | 0002898 A1 | 1/2000 |
| WO | 0065467 A1 | 11/2000 |
| WO | 02062819 A2 | 8/2002 |
| WO | 2010128098 A1 | 11/2010 |
| WO | 2013108254 A1 | 7/2013 |
| WO | 2014130949 A1 | 8/2014 |
| WO | 2019058367 A1 | 3/2019 |

OTHER PUBLICATIONS

Sun et al. Effects of Camptothecin Conjugated to a Somatostatin Analog Vector on Growth of Tumor Cell Lines in Culture and Related Tumors in Rodents. Drug Delivery, 11:231-238, 2004 (Year: 2004).*
Wang et al. Pharmacological properties of hydrophilic and lipophilic derivatives octreotate. Nuclear Medicine and Biology 31 (2004) 21-30 (Year: 2004).*
Porras et al. Somatostatin Analogs in Clinical Practice: A Review. Int J Mol Sci. Mar. 2020; 21(5): 1682 (Year: 2020).*
Afargan et al., (2001) Novel long-acting somatostatin analog with endocrine selectivity: potent suppression of growth hormone but not of insulin. Endocrinology 142(1): 477-486.
Artursson (1989) Epithelial transport of drugs in cell culture. I: A model for studying the passive diffusion of drugs over intestinal absorptive (Caco-2) cells. J Pharm Sci 79(6): 476-482.
Artursson and Karlsson (1991) Correlation between oral drug absorption in humans and apparent drug permeability coefficients in human intestinal epithelial (Caco-2) cells. Biochem Biophys Res Commun 175(3): 880-885.
Aumailley et al., (1991) Arg-Gly-Asp constrained within cyclic pentapeptides. Strong and selective inhibitors of cell adhesion to vitronectin and laminin fragment P1. FEBS Lett 291(1): 50-54.
Bauer et al., (1982) SMS 201-995: a very potent and selective octapeptide analogue of somatostatin with prolonged action. Life Sci 31(11): 1133-1140.

(Continued)

*Primary Examiner* — James H Alstrum-Acevedo
*Assistant Examiner* — Mercy H Sabila
(74) *Attorney, Agent, or Firm* — J.A. Lindeman & Co., PLLC; Stephen Bellum

(57) ABSTRACT

The present invention provides prodrugs of somatostatin peptide and peptide analogs that are tissue permeable and oral bioavailable and enable activity of the somatostatin analog at the circulation or target tissue after cleavage of charge-masking lipophilic moieties. Pharmaceutical compositions comprising these prodrugs and their use in therapy and diagnosis are also provided.

19 Claims, 1 Drawing Sheet
Specification includes a Sequence Listing.

(56) References Cited

OTHER PUBLICATIONS

Beck et al., (2012) Intestinal permeability of cyclic peptides: common key backbone motifs identified. J Am Chem Soc 134(29): 12125-12133 with Supporting Information.
Becker et al., (2015) Metabolism and disposition of the αv-integrin β3/β5 receptor antagonist cilengitide, a cyclic polypeptide, in humans. J Clin Pharmacol 55(7): 815-824.
Bernkop-Schnürch and Schmitz (2007) Presystemic metabolism of orally administered peptide drugs and strategies to overcome it. Curr Drug Metab 8(5): 509-517.
Biron et al., (2008) Improving oral bioavailability of peptides by multiple N-methylation: somatostatin analogues. Angew Chem Int Ed Engl 47(14): 2595-2599 with Supporting Information.
Bochen et al., (2013) Biselectivity of isoDGR peptides for fibronectin binding integrin subtypes α5β1 and αvβ6: conformational control through flanking amino acids. J Med Chem 56(4): 1509-1519 with Supporting Information.
Bock et al., (2013) Getting in shape: controlling peptide bioactivity and bioavailability using conformational constraints. ACS Chem Biol 8(3): 488-499.
Bousquet et al., (2001) Antiproliferative Effect of Somatostatin and Analogs. Chemotherapy 47(suppl 2): 30-39.
Chatterjee et al., (2008) N-methylation of peptides: a new perspective in medicinal chemistry. Acc Chem Res 41(10): 1331-1342.
Chatterjee et al., (2012) Synthesis of N-methylated cyclic peptides. Nat Protoc 7(3): 432-444.
Cherniakov et al., (2015) Self-nano-emulsifying drug delivery systems: an update of the biopharmaceutical aspects. Expert Opin Drug Deliv 12(7): 1121-1133.
Cherniakov et al., (2017) The effect of Pro NanoLipospheres (PNL) formulation containing natural absorption enhancers on the oral bioavailability of delta-9-tetrahydrocannabinol (THC) and cannabidiol (CBD) in a rat model. Eur J Pharm Sci 109: 21-30.
Craik et al., (2013) The future of peptide-based drugs. Chem Biol Drug Des 81(1): 136-147.
Dechantsreiter et al., (1999) N-Methylated cyclic RGD peptides as highly active and selective alpha(V)beta(3) integrin antagonists. J Med Chem 42(16): 3033-3040 with Supporting Information.
Dong et al., (2017) Force interacts with macromolecular structure in activation of TGF-β Nature 542(7639): 55-69.
Eisert et al., (2010) Dabigatran: an oral novel potent reversible nonpeptide inhibitor of thrombin. Arterioscler Thromb Vasc Biol 30(10): 1885-1889.
Falb et al., (2001) A bicyclic and hsst2 selective somatostatin analogue: design, synthesis, conformational analysis and binding. Bioorg Med Chem 9(12): 3255-3264.
Frank et al., (2010) Conformational control of integrin-subtype selectivity in isoDGR peptide motifs: a biological switch. Angew Chem Int Ed Engl 49(48): 9278-9281.
Friedler et al., (1998) Backbone cyclic peptide, which mimics the nuclear localization signal of human immunodeficiency virus type 1 matrix protein, inhibits nuclear import and virus production in nondividing cells. Biochemistry 37(16): 5616-5622.
Friesner et al., (2004) Glide: a new approach for rapid, accurate docking and scoring. 1. Method and assessment of docking accuracy. J Med Chem 47(7): 1739-1749.
Fuselier et al., (2003) An adjustable release rate linking strategy for cytotoxin-peptide conjugates. Bioorg Med Chem Lett 13(5): 799-803.
Gilon et al., (1991) Backbone cyclization: A new method for conferring conformational constraint on peptides. Biopolymers 31(6): 745-750.
Gilon et al., (1998) A backbone-cyclic, receptor 5-selective somatostatin analogue: synthesis, bioactivity, and nuclear magnetic resonance conformational analysis. J Med Chem 41(6): 919-929.
Greenwood et al., (2010) Towards the comprehensive, rapid, and accurate prediction of the favorable tautomeric states of drug-like molecules in aqueous solution. J Comput Aided Mol Des 24(6-7): 591-604.
Grozinsky-Glasberg et al., (2008) Somatostatin analogues in the control of neuroendocrine tumours: efficacy and mechanisms. Endocr Relat Cancer 15(3): 701-720.
Halgren et al., (2004) Glide: a new approach for rapid, accurate docking and scoring. 2. Enrichment factors in database screening. J Med Chem 47(7): 1750-1759.
Hamman et al., (2005) Oral delivery of peptide drugs: barriers and developments. BioDrugs 19(3): 165-177.
Han and Amidon (2000) Targeted prodrug design to optimize drug delivery. AAPS PharmSci 2(1): E6; 11 pages.
Harder et al., (2016) OPLS3: A Force Field Providing Broad Coverage of Drug-like Small Molecules and Proteins. J Chem Theory Comput 12(1): 281-296.
Haubner et al., (1997) Stereoisomeric Peptide Libraries and Peptidomimetics for Designing Selective Inhibitors of the αvβ3 Integrin for a New Cancer Therapy. Angewandte Chemie International Edition in English 36(13-14): 1374-1389.
Hayashi et al., (1998) GPIIb/IIIa integrin antagonists with the new conformational restriction unit, trisubstituted beta-amino acid derivatives, and a substituted benzamidine structure. J Med Chem 41(13): 2345-2360 with Supporting Information.
Heron et al., (1993) Pharmacokinetics and efficacy of a long-acting formulation of the new somatostatin analog BIM 23014 in patients with acromegaly. J Clin Endocrinol Metab 76(3): 721-727.
Hess et al., (2008) Backbone cyclic peptidomimetic melanocortin-4 receptor agonist as a novel orally administrated drug lead for treating obesity. J Med Chem 51(4): 1026-1034.
Hoole and West (2016) Bivalirudin in the treatment of acute coronary syndrome. BMJ 352: i86; 2 pages.
Hruby and Baise (2000) Conformational and topographical considerations in designing agonist peptidomimetics from peptide leads. Curr Med Chem 7(9): 945-970.
Hubatsch et al., (2007) Determination of drug permeability and prediction of drug absorption in Caco-2 monolayers. Nat Protoc 2(9): 2111-2119.
Hunter et al., (1993) Drug absorption limited by P-glycoprotein-mediated secretory drug transport in human intestinal epithelial Caco-2 cell layers. Pharm Res 10(5): 743-749.
International Union of Pure and Applied Chemistry (IUPAC) and International Union of Biochemistry (IUB), Joint Commission on Biochemical Nomenclature (JCBN); (1984) Nomenclature and symbolism for amino acids and peptides (Recommendations 1983). Pure & Appl Chem 56(5): 595-624.
Jornada et al., (2015) The Prodrug Approach: A Successful Tool for Improving Drug Solubility. Molecules 21(1): 42; 31 pages.
Ju et al., (2008) Stereoretentive synthesis and chemoselective amide-forming ligations of C-terminal peptide alpha-ketoacids. J Am Chem Soc 130(13): 4253-4255.
Kansy et al., (1998) Physicochemical High Throughput Screening: Parallel Artificial Membrane Permeation Assay in the Description of Passive Absorption Processes. J Med Chem 41(7): 1007-1010 with Supporting Information.
Kansy et al., (2004) Advances in screening for membrane permeability: high-resolution PAMPA for medicinal chemists. Drug Discovery Today: Technologies 1(4): 349-355.
Kapp et al., (2013) Integrin modulators: a patent review. Expert Opin Ther Pat 23(10): 1273-1295.
Kapp et al., (2016) Small Cause, Great Impact: Modification of the Guanidine Group in the RGD Motif Controls Integrin Subtype Selectivity. Angew Chem Int Ed Engl 55(4): 1540-1543 with Supporting Information.
Kapp et al., (2017) A Comprehensive Evaluation of the Activity and Selectivity Profile of Ligands for RGD-binding Integrins. Sci Rep 7: 39805; 13 pages.
Kessler H (2017); Design of an orally available peptide with biological activity. Presented at 38th Max-Bergmann-Conferencem Achalm (Reutlingen), Germany; Sep. 24-27, 2017. 52 pages.
Kumar et al., (1999) Subtype-selective expression of the five somatostatin receptors (hSSTR1-5) in human pancreatic slet cells: a quantitative double-label immunohistochemical analysis. Diabetes 48(1): 77-85.
Kumar et al., (2010) Caco-2 cell lines in drug discovery—an updated perspective. J Basic Clin Pharm 1(2): 63-69.

(56) References Cited

OTHER PUBLICATIONS

Lahlou et al., (2004) Molecular Signaling of Somatostatin Receptors. Annals of the New York Academy of Sciencesvol. 1014(1): 121-131.
Lambert et al., (2001) The synthesis of cyclic peptides. J Chem Soc Perkin Trans 1:471-484.
Lamberts et al., (1996) Octreotide. N Engl J Med 334(4): 246-254.
Ley et al., (2016) Integrin-based therapeutics: biological basis, clinical use and new drugs. Nat Rev Drug Discov 15(3): 173-183.
Linde et al., (2008) Structure-activity relationship and metabolic stability studies of backbone cyclization and N-methylation of melanocortin peptides. Biopolymers 90(5): 671-682.
Lipinski et al., (2001) Experimental and computational approaches to estimate solubility and permeability in drug discovery and development settings. Adv Drug Deliv Rev 46(1-3): 3-26.
Luhn et al., (2012) Dissolution Profile of Novel Composite Pellet Cores Based on Different Ratios of Microcrystalline Cellulose and Isomalt. Journal of Pharmaceutical Sciences 101(8): 2675-2680.
Marelli et al., (2015) cis-Peptide Bonds: A Key for Intestinal Permeability of Peptides? Chemistry 21(43): 15148-15152 with Supporting Information.
Marelli et al., (2015) Enantiomeric cyclic peptides with different Caco-2 permeability suggest carrier-mediated transport. Chemistry 21(22): 8023-8027 with Supporting Information.
Mas-Moruno et al., (2010) Cilengitide: the first anti-angiogenic small molecule drug candidate design, synthesis and clinical evaluation. Anticancer Agents Med Chem 10(10): 753-768.
Mezey et al., (1998) Cell specific expression of the sst2A and sst5 somatostatin receptors in the rat anterior pituitary. Endocrinology 139(1): 414-419.
Mitra et al., (1999) Colocalization of somatostatin receptor sst5 and insulin in rat pancreatic beta-cells. Endocrinology 140(8): 3790-3796.
Muñoz-Félix et al., (2017); Low doses of a new orally administered cyclic RGD peptide prodrug 29P increases and angiogenesis and is a powerful tool for vascular promotion cancer therapy. Presented at the 1st Crick Meeting in London, Sep. 24-26, 2017. 1 page.
Nabors et al., (2015) Two cilengitide regimens in combination with standard treatment for patients with newly diagnosed glioblastoma and unmethylated MGMT gene promoter: results of the open-label, controlled, randomized phase II Core study. Neuro Oncol 17(5): 708-717.
Naoum et al., (2017) DMAP-assisted sulfonylation as an efficient step for the methylation of primary amine motifs on solid support. Beilstein J Org Chem 13: 806-816.
Oberg (2004) Future aspects of somatostatin-receptor-mediated therapy. Neuroendocrinology 80 Suppl 1: 57-61.
Ovadia et al., (2010) Improvement of drug-like properties of peptides: the somatostatin paradigm. Expert Opin Drug Discov 5(7): 655-671.
Ovadia et al., (2010) The effect of backbone cyclization on PK/PD properties of bioactive peptide-peptoid hybrids: the melanocortin agonist paradigm. Bioorg Med Chem 18(2): 580-589.
Ovadia et al., (2011) The effect of multiple N-methylation on intestinal permeability of cyclic hexapeptides. Mol Pharm 8(2): 479-487.
Patel et al., (1990) Mechanism of action of somatostatin: An overview of receptor function and studies of the molecular characterization and purification of somatostatin receptor proteins. Metabolism 39(9, Suppl 2): 63-69.
Picariello et al., (2016) Use of brush border membrane vesicles to simulate the human intestinal digestion. Food Research International 88(Part B): 327-335.
Pillai and Panchagnula (2001) Polymers in drug delivery. Curr Opin Chem Biol 5(4): 447-451.
Pollak and Schally (1998) Mechanisms of antineoplastic action of somatostatin analogs. Proc Soc Exp Biol Med 217(2): 143-152.
Powell (1993) Chapter 30. Peptide Stability in Drug Development: in vitro Peptide Degradation in Plasma and Serum. Annual Reports in Medicinal Chemistry 28: 285-294.
Reardon et al., (2011) Cilengitide: an RGD pentapeptide $\alpha v\beta 3$ and $\alpha v\beta 5$ integrin inhibitor in development for glioblastoma and other malignancies. Future Oncol 7(3): 339-354.
Reichlin (1983) Somatostatin. N Engl J Med 309(24): 1495-1501.
Renukuntla et al., (2013) Approaches for enhancing oral bioavailability of peptides and proteins. Int J Pharm 447(1-2): 75-93.
Reynolds et al., (2009) Stimulation of tumor growth and angiogenesis by low concentrations of RGD-mimetic integrin inhibitors. Nat Med 15(4): 392-400.
Sastry et al., (2013) Protein and ligand preparation: parameters, protocols, and influence on virtual screening enrichments. J Comput Aided Mol Des 27(3): 221-234.
Scarpignato and Pelosini (2001) Somatostatin Analogs for Cancer Treatment and Diagnosis: An Overview. Chemotherapy 47(suppl 2): 1-29.
Schally (1988) Oncological applications of somatostatin analogues. Cancer Res 48(24 Pt 1): 6977-6985.
Schumacher-Klinger et al., (2018) Enhancing Oral Bioavailability of Cyclic RGD Hexa-peptides by the Lipophilic Prodrug Charge Masking Approach: Redirection of Peptide Intestinal Permeability from a Paracellular to Transcellular Pathway. Mol Pharm 15(8): 3468-3477.
Shan et al., (1997) Prodrug strategies based on intramolecular cyclization reactions. J Pharm Sci 86(7): 765-767.
Shelley et al., (2007) Epik: a software program for pK(a) prediction and protonation state generation for drug-like molecules. J Comput Aided Mol Des 21(12): 681-691.
Simplício et al., (2008) Prodrugs for amines. Molecules 13(3): 519-547.
Springer et al., (2008) Structural basis for distinctive recognition of fibrinogen yC peptide by the platelet integrin $\alpha IIb\beta 3$. J Cell Biol 182(4): 791-800.
Srinivasan et al., (2015) TEER Measurement Techniques for In Vitro Barrier Model Systems. J Lab Autom 20(2): 107-126.
Sun et al., (2007) A conjugate of camptothecin and a somatostatin analog against prostate cancer cell invasion via a possible signaling pathway involving PI3K/Akt, $\alpha V\beta 3/\alpha V\beta 5$ and MMP-2/-9. Cancer Letters 246(1-2): 157-166.
Takagi et al., (2003) Structure of integrin alpha5beta1 in complex with fibronectin. The EMBO Journal 22(18): 4607-4615.
Tsomaia (2015) Peptide therapeutics: targeting the undruggable space. Eur J Med Chem 94: 459-470.
Van Ryn et al., (2013) The discovery of dabigatran etexilate. Front Pharmacol 4: 12; 8 pages.
Veber et al., (1981) A potent cyclic hexapeptide analogue of somatostatin. Nature 292(5818): 55-58.
Wang and Craik (2016) Cyclic peptide oral bioavailability: Lessons from the past. Biopolymers 106(6): 901-909.
Wang et al., (2004) Pharmacological properties of hydrophilic and lipophilic derivatives of octreotate. Nucl Med Biol 31(1): 21-30.
Weide T., Modlinger A., Kessler H. (2006) Spatial Screening for the Identification of the Bioactive Conformation of Integrin Ligands. In: Peters T. (eds) Bioactive Conformation I. Topics in Current Chemistry, vol. 272. Springer, Berlin, Heidelberg; pp. 1-50.
Weinmüller et al., (2017) Overcoming the Lack of Oral Availability of Cyclic Hexapeptides: Design of a Selective and Orally Available Ligand for the Integrin $\alpha v\beta 3$. Angew Chem Int Ed Engl 56(51): 16405-16409 with Supporting Information.
Wong et al., (2015) Dual-action combination therapy enhances angiogenesis while reducing tumor growth and spread. Cancer Cell 27(1): 123-137 with Supporting Information.
Wong et al., (2016) Exploring Novel Methods for Modulating Tumor Blood Vessels in Cancer Treatment. Curr Biol 26(21): R1161-R1166.
Xiong et al., (2002) Crystal structure of the extracellular segment of integrin alpha Vbeta3 in complex with an Arg-Gly-Asp ligand. Science 296(5565): 151-155.
Xiong et al., (2009) Crystal structure of the complete integrin alphaVbeta3 ectodomain plus an alpha/beta transmembrane fragment. J Cell Biol 186(4): 589-600.
Zablocki et al., (1995) Potent in vitro and in vivo inhibitors of platelet aggregation based upon the Arg-Gly-Asp sequence of fibrinogen. (Aminobenzamidino)succinyl (ABAS) series of orally

(56) References Cited

OTHER PUBLICATIONS active fibrinogen receptor antagonists. J Med Chem 38(13): 2378-2394 with Supporting Information.

Zimmer et al., (1993) "Head-to-Tail" Cyclization of Hexapeptides Using Different Coupling Reagents. Liebigs Annalen der Chemie 1993(5): 497-501.

* cited by examiner

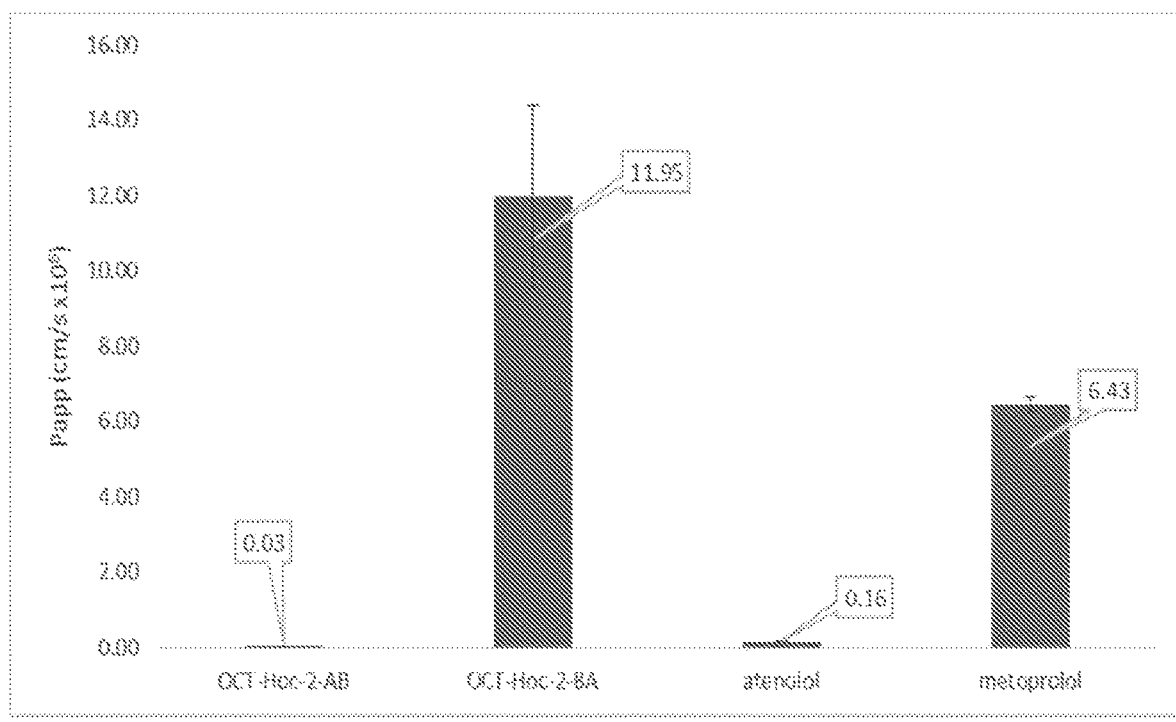

SEQUENCE LISTING

```
<160> NUMBER OF SEQ ID NOS: 23

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Phe
<220> FEATURE:
<221> NAME/KEY: DISULFID
<222> LOCATION: (2)..(7)
<223> OTHER INFORMATION: bridge
<220> FEATURE:
<221> NAME/KEY: MISC_FEATURE
<222> LOCATION: (4)..(4)
<223> OTHER INFORMATION: D-Trp
<220> FEATURE:
```

```
<221> NAME/KEY: MISC_FEATURE
<222> LOCATION: (8)..(8)
<223> OTHER INFORMATION: (ol) = alcohol C termuinus

<400> SEQUENCE: 1

Phe Cys Phe Trp Lys Thr Cys Thr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: X = D-2 naphthylalanine
<220> FEATURE:
<221> NAME/KEY: DISULFID
<222> LOCATION: (2)..(7)
<223> OTHER INFORMATION: bridge
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (8)..(8)
<223> OTHER INFORMATION: AMIDATION

<400> SEQUENCE: 2

Xaa Cys Tyr Trp Lys Val Cys Thr
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4Abu, GABA
<220> FEATURE:
<221> NAME/KEY: MOD_RES
<222> LOCATION: (1)..(8)
<223> OTHER INFORMATION: backbone-to-end cyclization between the
      N-alpha-omega-functionalized derivative of GlyC3 and the
      N-terminus
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (8)..(8)
<223> OTHER INFORMATION: AMIDATION
<220> FEATURE:
<221> NAME/KEY: MOD_RES
<222> LOCATION: (8)..(8)
<223> OTHER INFORMATION: GlyC3 building unit

<400> SEQUENCE: 3

Xaa Phe Trp Trp Lys Thr Phe Gly
1               5

<210> SEQ ID NO 4
<211> LENGTH: 6
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MOD_RES
<222> LOCATION: (1)..(1)
<223> OTHER INFORMATION: (2-aminoethyl-carbamoyl)-Hydroxyproline
<220> FEATURE:
<221> NAME/KEY: MOD_RES
<222> LOCATION: (1)..(6)
<223> OTHER INFORMATION: head-to-tail cyclization
<220> FEATURE:
<221> NAME/KEY: MOD_RES
<222> LOCATION: (2)..(2)
<223> OTHER INFORMATION: PhenylGlycine, Phg
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (5)..(5)
<223> OTHER INFORMATION: Tyr(Bzl)

<400> SEQUENCE: 4

Xaa Xaa Trp Lys Tyr Phe
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide

<400> SEQUENCE: 5

Phe Trp Lys Thr
1

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: D-Trp

<400> SEQUENCE: 6

Phe Trp Lys Thr
1

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(6)
<223> OTHER INFORMATION: head-to-tail-cyclization
<220> FEATURE:
<221> NAME/KEY: MOD_RES
<222> LOCATION: (3)..(3)
<223> OTHER INFORMATION: D-Trp

<400> SEQUENCE: 7

Pro Phe Trp Lys Thr Phe
1               5
```

-continued

```
<210> SEQ ID NO 8
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(6)
<223> OTHER INFORMATION: head-to-tail cyclization
<220> FEATURE:
<221> NAME/KEY: MOD_RES
<222> LOCATION: (3)..(3)
<223> OTHER INFORMATION: N-methyl D-Trp
<220> FEATURE:
<221> NAME/KEY: MOD_RES
<222> LOCATION: (4)..(4)
<223> OTHER INFORMATION: N-methyl Lys
<220> FEATURE:
<221> NAME/KEY: MOD_RES
<222> LOCATION: (6)..(6)
<223> OTHER INFORMATION: N-methyl Phe

<400> SEQUENCE: 8

Pro Phe Trp Lys Thr Phe
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PheN2 building unit
<220> FEATURE:
<221> NAME/KEY: MOD_RES
<222> LOCATION: (1)..(6)
<223> OTHER INFORMATION: backbone cyclization between the N-alpha-omega-
      functionalized derivative of X1 and the N-alpha-omega-
      functionalized derivative of X6
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (6)..(6)
<223> OTHER INFORMATION: PheC3 building unit
<220> FEATURE:
<221> NAME/KEY: MOD_RES
<222> LOCATION: (7)..(7)
<223> OTHER INFORMATION: AMIDATION

<400> SEQUENCE: 9

Phe Tyr Trp Lys Val Phe Thr
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PheC3 building unit
<220> FEATURE:
<221> NAME/KEY: MOD_RES
<222> LOCATION: (1)..(9)
<223> OTHER INFORMATION: backbone cyclization between the N-alpha-omega-
      functionalized derivative of X1 and the N-alpha-omega-
```

```
        functionalized derivative of X9
<220> FEATURE:
<221> NAME/KEY: DISULFID
<222> LOCATION: (2)..(7)
<223> OTHER INFORMATION: bridge
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (9)..(9)
<223> OTHER INFORMATION: PheN3 building unit
<220> FEATURE:
<221> NAME/KEY: MOD_RES
<222> LOCATION: (9)..(9)
<223> OTHER INFORMATION: AMIDATION

<400> SEQUENCE: 10

Phe Cys Phe Trp Lys Thr Cys Phe Phe
1               5

<210> SEQ ID NO 11
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-METHYL D-Trp
<220> FEATURE:
<221> NAME/KEY: MOD_RES
<222> LOCATION: (2)..(2)
<223> OTHER INFORMATION: N-METHYL Lys
<220> FEATURE:
<221> NAME/KEY: MOD_RES
<222> LOCATION: (4)..(4)
<223> OTHER INFORMATION: N-METHYL Phe

<400> SEQUENCE: 11

Trp Lys Thr Phe
1

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(6)
<223> OTHER INFORMATION: head-to-tail cyclization
<220> FEATURE:
<221> NAME/KEY: MOD_RES
<222> LOCATION: (3)..(3)
<223> OTHER INFORMATION: N-methyl D-Trp
<220> FEATURE:
<221> NAME/KEY: MOD_RES
<222> LOCATION: (4)..(4)
<223> OTHER INFORMATION: N-methyl Lys
<220> FEATURE:
<221> NAME/KEY: MOD_RES
<222> LOCATION: (6)..(6)
<223> OTHER INFORMATION: N-methyl Phe

<400> SEQUENCE: 12

Phe Trp Trp Lys Thr Phe
1               5

<210> SEQ ID NO 13
```

```
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(6)
<223> OTHER INFORMATION: Backbone-to-end cyclization between the
      N-alpha-omega-functionalized derivative of X6 and the N terminus
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Lys
<220> FEATURE:
<221> NAME/KEY: MOD_RES
<222> LOCATION: (6)..(6)
<223> OTHER INFORMATION: AMIDATION
<220> FEATURE:
<221> NAME/KEY: MOD_RES
<222> LOCATION: (6)..(6)
<223> OTHER INFORMATION: PheC2 building unit

<400> SEQUENCE: 13

Phe Phe Phe Trp Lys Phe
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PheC1 building unit
<220> FEATURE:
<221> NAME/KEY: MOD_RES
<222> LOCATION: (1)..(6)
<223> OTHER INFORMATION: backbone cyclization between the N-alpha-omega-
      functionalized derivative of X1 and the N-alpha-omega-
      functionalized derivative of X6
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (6)..(6)
<223> OTHER INFORMATION: AMIDATION
<220> FEATURE:
<221> NAME/KEY: MOD_RES
<222> LOCATION: (6)..(6)
<223> OTHER INFORMATION: PheN2 building unit

<400> SEQUENCE: 14

Phe Phe Phe Trp Lys Phe
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PheC1 building unit
<220> FEATURE:
```

```
<221> NAME/KEY: MOD_RES
<222> LOCATION: (1)..(6)
<223> OTHER INFORMATION: backbone cyclization between the N-alpha-omega-
      functionalized derivative of X1 and the N-alpha-omega-
      functionalized derivative of X6
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (5)..(5)
<223> OTHER INFORMATION: D-Lys
<220> FEATURE:
<221> NAME/KEY: MOD_RES
<222> LOCATION: (6)..(6)
<223> OTHER INFORMATION: PheN2 building unit
<220> FEATURE:
<221> NAME/KEY: MOD_RES
<222> LOCATION: (6)..(6)
<223> OTHER INFORMATION: AMIDATION

<400> SEQUENCE: 15

Phe Phe Phe Trp Lys Phe
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PheN2 building unit
<220> FEATURE:
<221> NAME/KEY: MOD_RES
<222> LOCATION: (1)..(6)
<223> OTHER INFORMATION: backbone cyclization between the N-alpha-omega-
      functionalized derivative of X1 and the N-alpha-omega-
      functionalized derivative of X6
<220> FEATURE:
<221> NAME/KEY: MOD_RES
<222> LOCATION: (3)..(3)
<223> OTHER INFORMATION: D-2-naphtylalanine
<220> FEATURE:
<221> NAME/KEY: MOD_RES
<222> LOCATION: (6)..(6)
<223> OTHER INFORMATION: GlyC2 building unit
<220> FEATURE:
<221> NAME/KEY: MOD_RES
<222> LOCATION: (7)..(7)
<223> OTHER INFORMATION: AMIDATION

<400> SEQUENCE: 16

Phe Tyr Xaa Lys Val Gly Thr
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PheN2 building unit
<220> FEATURE:
<221> NAME/KEY: MOD_RES
<222> LOCATION: (1)..(6)
<223> OTHER INFORMATION: backbone cyclization between the N-alpha-omega-
      functionalized derivative of X1 and the N-alpha-omega-
      functionalized derivative of X6
```

-continued

```
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (6)..(6)
<223> OTHER INFORMATION: GlyC2 building unit
<220> FEATURE:
<221> NAME/KEY: MOD_RES
<222> LOCATION: (7)..(7)
<223> OTHER INFORMATION: AMIDATION
<220> FEATURE:
<221> NAME/KEY: MOD_RES
<222> LOCATION: (7)..(7)
<223> OTHER INFORMATION: 2-naphtylalanine

<400> SEQUENCE: 17

Phe Tyr Trp Lys Val Gly Xaa
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PheN2 building unit
<220> FEATURE:
<221> NAME/KEY: MOD_RES
<222> LOCATION: (1)..(7)
<223> OTHER INFORMATION: backbone cyclization between the N-alpha-omega-
      functionalized derivative of X1 and the N-alpha-omega-
      functionalized derivative of X7
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (7)..(7)
<223> OTHER INFORMATION: GlyC2 building unit
<220> FEATURE:
<221> NAME/KEY: MOD_RES
<222> LOCATION: (7)..(7)
<223> OTHER INFORMATION: AMIDATION

<400> SEQUENCE: 18

Phe Tyr Trp Lys Val Val Gly
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PheN2 building unit
<220> FEATURE:
<221> NAME/KEY: MOD_RES
<222> LOCATION: (1)..(7)
<223> OTHER INFORMATION: backbone cyclization between the N-alpha-omega-
      functionalized derivative of X1 and the N-alpha-omega-
      functionalized derivative of X7
<220> FEATURE:
<221> NAME/KEY: MOD_RES
<222> LOCATION: (3)..(3)
<223> OTHER INFORMATION: D-Trp
<220> FEATURE:
```

```
<221> NAME/KEY: MOD_RES
<222> LOCATION: (6)..(6)
<223> OTHER INFORMATION: Naphtylalanine
<220> FEATURE:
<221> NAME/KEY: MOD_RES
<222> LOCATION: (7)..(7)
<223> OTHER INFORMATION: GlyC2 building unit
<220> FEATURE:
<221> NAME/KEY: MOD_RES
<222> LOCATION: (7)..(7)
<223> OTHER INFORMATION: AMIDATION

<400> SEQUENCE: 19

Phe Tyr Trp Lys Ser Xaa Gly
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PheN2 building unit
<220> FEATURE:
<221> NAME/KEY: MOD_RES
<222> LOCATION: (1)..(7)
<223> OTHER INFORMATION: backbone cyclization between the N-alpha-omega-
      functionalized derivative of X1 and the N-alpha-omega-
      functionalized derivative of X7
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (6)..(6)
<223> OTHER INFORMATION: 2-naphtylalanine
<220> FEATURE:
<221> NAME/KEY: MOD_RES
<222> LOCATION: (7)..(7)
<223> OTHER INFORMATION: GlyC2 building unit
<220> FEATURE:
<221> NAME/KEY: MOD_RES
<222> LOCATION: (7)..(7)
<223> OTHER INFORMATION: AMIDATION

<400> SEQUENCE: 20

Phe Phe Trp Lys Thr Xaa Gly
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(8)
<223> OTHER INFORMATION: backbone cyclization with disulfide bond
      between the N-alpha-omega-S-functionalized derivative of X8 and
      the side chain of the X1 Cysteine
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (8)..(8)
<223> OTHER INFORMATION: GlyS2 building unit
<220> FEATURE:
<221> NAME/KEY: MOD_RES
```

```
<222> LOCATION: (8)..(8)
<223> OTHER INFORMATION: AMIDATION

<400> SEQUENCE: 21

Cys Phe Trp Trp Lys Thr Phe Gly
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (2)..(9)
<223> OTHER INFORMATION: Backbone cyclization with disulfide bridge
      between the N-alpha-omega-S-functionalized derivative of X9 and
      the side chain of the X2 Cys residue
<220> FEATURE:
<221> NAME/KEY: MOD_RES
<222> LOCATION: (5)..(5)
<223> OTHER INFORMATION: D-Trp
<220> FEATURE:
<221> NAME/KEY: MOD_RES
<222> LOCATION: (9)..(9)
<223> OTHER INFORMATION: GlyS2 building unit
<220> FEATURE:
<221> NAME/KEY: MOD_RES
<222> LOCATION: (9)..(9)
<223> OTHER INFORMATION: AMIDATION

<400> SEQUENCE: 22

Phe Cys Phe Trp Trp Lys Thr Phe Gly
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: CARBOHYD
<222> LOCATION: (1)..(1)
<223> OTHER INFORMATION: Galactose
<220> FEATURE:
<221> NAME/KEY: MOD_RES
<222> LOCATION: (1)..(1)
<223> OTHER INFORMATION: Dbu - 2,4 diaminobutiric acid
<220> FEATURE:
<221> NAME/KEY: MOD_RES
<222> LOCATION: (1)..(8)
<223> OTHER INFORMATION: Backbone cyclization between the N-alpha-omega-
      functionalized derivative of X8 and the free amino group of X1
<220> FEATURE:
<221> NAME/KEY: MOD_RES
<222> LOCATION: (4)..(4)
<223> OTHER INFORMATION: D-Trp
<220> FEATURE:
<221> NAME/KEY: MOD_RES
<222> LOCATION: (8)..(8)
<223> OTHER INFORMATION: GlyC3 building unit
```

```
-continued

<220> FEATURE:
<221> NAME/KEY: MOD_RES
<222> LOCATION: (8)..(8)
<223> OTHER INFORMATION: AMIDATION

<400> SEQUENCE: 23

Xaa Phe Trp Trp Lys Thr Phe Gly
1               5
```

SOMATOSTATIN PRODRUGS

FIELD OF THE INVENTION

The present invention relates to methods for improving the permeability and oral bioavailability of somatostatin derivatives, to somatostatin prodrugs and to their use in therapy.

BACKGROUND OF THE INVENTION

Somatostatin is a peptide hormone involved in many different biological functions. The native somatostatin (SRIF, somatotropin release inhibitory factor), was found to have a cyclic structure joined by an intramolecular disulfide bond between two cysteine residues. In the human body, it is present in two forms, as somatostatin-14 and somatostatin-28 (14 and 28 amino acids, respectively) [1]. Somatostatin has a broad spectrum of biological actions, exerts suppressive effects on a large variety of cells, and appears to be an endogenous growth inhibitor [2]. The SRIF binds with high affinity to five different subtypes of specific SRIF receptors (SSTRs) on the cell surface, which belong to the G-protein-coupled receptor family (SSTR1, SSTR2, SSTR3, SSTR4 and SSTR5 [3,4]. SRIF acts as an important regulator of endocrine function by inhibiting the secretion of various hormones, such as growth hormone (GH) and gastrointestinal hormones [5]. In the pituitary gland, somatotropins have predominant expression of SSTR2 and SSTR5 receptors, indicating that these receptor subtypes may be involved in the regulation of GH secretion [6]. Furthermore, SSTR1 and SSTR5 receptors have been strongly co-localized with insulin in the pancreatic β-cells, and pancreatic α-cells are rich in SSTR2 [7,8]. In addition to their suppressive effects on secretory symptoms, somatostatin and somatostatin analogs appear to induce antiproliferative effect. Somatostatin and its analogs have antineoplastic activity in a variety of experimental tumor models in vitro and in vivo [9,10], turning them into promising candidates for drug development in the field of cancer therapy [11-13].

Despite the therapeutic potential, the very short half-life of the natural compound (about 3 minutes in blood) has resulted in the development of synthetic analogs: short acting (octreotide, which needs to be administered subcutaneously several times per day) or long acting (octreotide long-acting release, LAR and lanreotide autogel), with a monthly administration [14]. These analogs share with the native SRIF its pharmacophore, the essential four amino acid sequence Phe7-Trp8-Lys9-Thr10 (the numbering follows that of native SRIF) responsible for its biological activity [7]. The efforts to generate improved analogs led to reducing the molecular mass of the 14-amino-acid SRIF to octapeptides and hexapeptides and small molecules.

The major challenges in utilizing somatostatin derivatives for various therapeutic goals are overcoming the poor intestinal permeability.

Through the years, much effort has been made to develop somatostatin analogs with an improved pharmacokinetics (PK) profile (i.e., enhanced stability to biodegradation and oral bioavailability) and/or improved pharmacodynamics (PD) profile (i.e., analogs with modified sub-receptor selectivity). Most of the synthetic efforts have been focused on peptide side-chain modifications, peptide backbone modifications and changes in the bioactive sequence of the parent peptide (i.e., deletion/addition and substitution of amino acids) [15]. Linear peptides have many rapidly interconverting conformations and although slightly preferred conformations may be more populated in some cases, they are generally highly dependent on the environment. Conformationally constrained peptides have led to a revolution in ligand design. The impact of the implementation of such constraints on the overall structure as well as on ligand-receptor interactions is extensive. Restricted conformation may generate desired drug-like properties which include enhancement of ligand-receptor interaction and reduction of enzymatic susceptibility [16].

The most widely studied somatostatin analog is the cyclic peptide octreotide DPhe(Cys-Phe-DTrp-Lys-Thr-Cys)-Thr(ol) (SEQ ID NO: 1), [17]. In the case of octreotide, several chemical modifications have been made in order to improve its properties; i) shortening of the sequence to eight amino acids; ii) replacement of Trp8 with D-Trp8; iii) shifting of the disulfide bridge closer to the pharmacophore (amino acids 6-11) and iv) changing of the N-terminal and the C-terminal Phe to D-Phe and Thr into reduced threoninol, respectively, in order to reduce enzymatic cleavage [18]. These modifications did not alter octreotide poor degree of intestinal absorption; thus, it is administered parenterally.

In recent years, there have been tremendous advances in chemistry which have led to the development of very promising approaches aimed to develop peptide-based therapeutics, overcoming their natural low enzymatic stability and oral bioavailability while retaining, or even improving, their biological activity. Many chemical modifications have been used to develop a somatostatin analogue with improved PK/PD profile, head-to-tail-cyclization, backbone cyclization (BC) and N-methylation [1].

The poor metabolic stability of SRIF and lack of selectivity were addressed by several methods. For example, the cycloscan method which is based on the selection of backbone cyclic peptide(s) from rationally designed combinatorial library with conformational diversity. Backbone cyclization [19] is a general method by which conformational constraint is imposed on peptides [20]. In backbone cyclization, a peptidomimetic is formed by covalently interconnecting atoms in the backbone (N and/or C) of a target linear peptide to form a ring. The advantage of backbone cyclization over other modes of peptide cyclization is that cyclization is achieved mainly using backbone atoms and not side chains that are essential for biological activity. This method has been shown to dramatically enhance the metabolic stability of peptides in serum [21]. Backbone cyclized somatostatin analogs are disclosed for example in WO 99/65508 and WO98/04583. Another method involves "Spatial screening" end-to-end N-methylated cyclic penta- and hexa-peptides from focused combinatorial libraries with conformational diversity. This chemical modification, in which the amide proton is replaced by an N-methyl group, is known to naturally occur in a variety of peptides, including cyclosporine. N-Methylation has been used to produce peptides with improved intestinal and cellular permeability. Moreover, incorporation of N-methylated amino acids into the sequence of peptides was found to affect pharmacological properties, including binding affinity [22,23]. The methods above overcome the two major disadvantages of the standard cyclization strategies that result in loss of biological activity: (1) pharmacophoric side chains are often used for cyclization and/or these side chains must be replaces by residues that allow cyclization; and (2) restricting the conformational space of linear peptide by cyclization leads to many inactive cyclic peptides because they are unable to attain the proper bioactive conformation. Using these methods, multitude of peptides and active regions of proteins were successfully converted into metabolically stable, highly active and specific peptidomimetics (e.g. WO 2014/130949). However, the intestinal absorption was still insufficient as these approaches did not affect the permeability rate of the somatostatin peptides.

Prodrugs are poorly active or inactive compounds containing the parental compound that undergoes in vivo biotransformation through chemical or enzymatic cleavage, enabling the delivery of the active compound in an effective manner and amount thus overcoming pharmacokinetic, pharmacodynamic and toxicology challenges without permanently altering the pharmacological properties of the parental drug [24]. The features of an ideal prodrug include the following: (a) stability during the adsorption process (e.g. resistance to enzymatic degradation and inactivation by Cytochrome P450 (CYP); (b) weak or no activity; (c) aqueous solubility; (d) good permeability through intestinal or cellular membranes; (e) chemical stability at different pH values; (f) release of the parental drug by controlling the kinetics and site [25]. Prodrugs can be designed to serve several objectives. Carrier-linked prodrugs can be targeted to a specific site of action. For example, in cancer treatment studies, the parent drug is conjugated to a specific anti-tumor monoclonal antibody that would target certain cells [24]. Additionally, a prodrug can be designed to target specific tissues by drug activation of enzymes that are unique or present at a higher concentration in that tissue. For example, glycosidase and azo reductase activity of the colonic microflora offers an opportunity to design a colon-specific drug delivery system [24]. The prodrug approach can also be used to modify the physicochemical properties of peptide drugs to improve their passive membrane permeation. The major challenges in peptide membrane permeability via passive diffusion includes the peptide's high polarity, charge and hydrogen bond potential. Methods that can mask ionizable functional groups of a peptide can help reducing the polarity and charge of a peptide, and thus improve its membrane permeability [26].

There is an unmet need for tissue permeable and metabolic stable somatostatin derivatives that can be administered orally, eliminating the need for parenteral administration.

SUMMARY OF THE INVENTION

The present invention provides prodrugs of somatostatin and somatostatin derivatives that enables oral administration without losing activity or specificity. The prodrugs of the present invention contain moieties that mask charged groups of the peptide's sequence and increases its hydrophobicity and permeability through biological membranes and thus increase bioavailability of the somatostatin compound. According to the methods of the present invention, hydrophobic masking moieties are connected to the peptide's terminal and/or side chain via a cleavable linkage that allows selective removal and release of the active drug in the circulatory system or target tissue. None limiting examples of the present invention include Octreotide prodrugs having enhanced intestinal permeability via the transcellular pathway.

The major drawback of peptides in general and somatostatin derivatives specifically, as therapeutic entities is that they require parenteral administration due to their poor intestinal permeability that attributed mainly to the charged groups of their sequence. The present invention provides methods for improving passive membrane permeation of somatostatin compounds by providing prodrugs comprising masked ionizable (charged) functional groups. Masking of ionizable functional groups of a peptide sequence reduces the polarity and charge of a peptide, and together with the hydrophobic moiety attached improves its membrane permeability.

The invention thus provides compounds with increased oral availability while maintaining their activity in the target cells and tissues following transformation into active somatostatin forms.

Prodrugs according to the present invention are poorly active or inactive compounds containing the parental somatostatin that undergoes in vivo biotransformation through chemical or enzymatic cleavage, enabling the delivery of the active compound in an effective manner and amount thus overcoming pharmacokinetic, pharmacodynamic and toxicology challenges without permanently altering the pharmacological properties of the parental drug.

The present invention provides, according to one aspect, somatostatin prodrugs comprising a cyclic peptide sequence coupled to at least one charge-masking, permeability-enhancing lipophilic-carbamate moiety connected through a cleavable linkage to at least one terminal or charged side chain of the peptide.

The charge-masking permeability-enhancing moiety according to the present invention is coupled to the peptide's sequence directly or through a spacer or linker to form a cleavable linkage. According to some embodiments the cleavable linkage comprises a protease-specific cleavage site.

According to some embodiments, the permeability-enhancing moiety is a lipophilic alkyl oxycarbonyl moiety.

According to some embodiments, the permeability-enhancing moiety is a hexyloxycarbonyl (Hoc) moiety.

According to some embodiments, at least one positively charged group of the peptide sequence is masked with a hexyloxycarbonyl (Hoc) moiety. According to specific embodiments, two or more positively charged groups of the peptide sequence are masked with hexyloxycarbonyl (Hoc) moieties. According to specific embodiments, the prodrug comprises two hexyloxycarbonyl (Hoc) moieties.

According to some embodiments, at least one permeability-enhancing moiety is connected through a cleavable linkage to at least one terminal or charged side chain of the peptide, and at least one additional permeability-enhancing moiety is connected through a cleavable linkage to the nitrogen atom of a Tryptophan (Trp) side chain.

According to some embodiments, the prodrug comprises 5-15 amino acid residues. According to other embodiments the prodrug comprises of 5-7, 5-8, 5-9, 5-10, 5-11 or 5-12 amino acid residues. According to yet other embodiments, the prodrug comprises 6-12, 6-11, 6-10, 6-9 or 6-8 amino acid residues. Each possibility represents a separate embodiment of the present invention.

According to some embodiments, the prodrug comprises a somatostatin analog consisting of 5-12 amino acid residues. According to other embodiments, the prodrug comprises a somatostatin analog consisting of 5-10, 6-9 or 7-8 amino acid residues. According to some embodiments, the somatostatin analog consists of 6, 7, 8 or 9, 10 amino acid residues. Each possibility represents a separate embodiment of the present invention.

Any somatostatin compound, analog or derivative known in the art that comprises at least one charged residue, can be used to produce a prodrug according to the present invention.

According to some embodiments, the prodrug comprises a cyclic somatostatin analog having at least one modification relative to a parent somatostatin molecule (peptide or peptide analog), said at least one modification is selected from the group consisting of: deletion, substitution, methylation or addition of amino acids, and combinations thereof. Each possibility represents a separate embodiment of the present invention.

According to other embodiments, the at least one modification comprises modification of the C-terminus of the peptide. According to some specific embodiments, modification of the C-terminus results in an amidated, carboxylated or alcohol C-terminus.

According to yet other embodiments, the at least one modification is made to the backbone of the peptide or peptide analog, including but not limited to replacement of cyclization type, creation of cyclization and removal of cyclization.

Any type of cyclization may be added or replaced in the somatostatin peptides and analog of the prodrugs of the present invention, including but not limited to disulfide cyclization, backbone cyclization, and head-to tail cyclization.

According to some embodiments, the prodrug comprises a cyclic somatostatin analog having 1-2 modifications relative to the parent somatostatin molecule, said 1-2 modifications are selected from amino acid, terminal or backbone modifications.

According to some embodiments, the cyclic somatostatin analog is selected from the group consisting of octreotide (also known as sandostatin), having the sequence DPhe-(Cys-Phe-DTrp-Lys-Thr-Cys)-Thr(ol) (SEQ ID NO: 1), somatuline (also known as lanreotide), having the sequence D2Nal-(Cys-Tyr-DTrp-Lys-Val-Cys)-Thr-NH$_2$ (SEQ ID NO: 2), PTR-3173 (also known as Somatoprim), having the sequence (GABA-Phe-Trp-DTrp-Lys-Thr-Phe-GlyC3)-NH$_2$ (SEQ ID NO: 3) and Pasireotide having the sequence Cyclo(-Hyp(2-aminoethyl-carbamoyl)-Phg-D-Trp-Lys-Tyr (Bzl)-Phe) (SEQ ID NO: 4).

According to some embodiments, the cyclic somatostatin analog comprises the sequence Phe-Trp-Lys-Thr (FWKT, SEQ ID NO: 5).

According to some embodiments, the cyclic somatostatin analog comprises at least one amino acid residue in D configuration.

According to some specific embodiments, the cyclic somatostatin analog comprises the sequence Phe-DTrp-Lys-Thr (FwKT, SEQ ID NO: 6).

According to some specific embodiments, the somatostatin prodrug comprises a sequence selected from FWKT (SEQ ID NO: 5) and FwKT (SEQ ID NO: 6), and at least one hexyloxycarbonyl moiety coupled to an amine group of the peptide's terminus or of an amino acid side chain.

According to some embodiments, the prodrug comprises a somatostatin analog comprising at least one N-methylated amino acid residue.

According to yet other embodiments, the cyclic somatostatin analog comprises 2 or 3 N-methylated amino acid residues.

According to some specific embodiments, the prodrug comprises the somatostatin analog octreotide (SEQ ID NO: 1), or a derivative thereof.

According to some embodiments, the octreotide derivative comprises a modified C-terminus, such as amidated or carboxy terminus.

According to some embodiments, the somatostatin prodrug comprises an octreotide derivative having 1 or 2 substitutions, additions, deletions or combinations thereof, to the SEQ ID NO: 1.

The invention thus provides, according to some embodiments an octreotide prodrug comprising the sequence DPhe-(Cys-Phe-DTrp-Lys-Thr-Cys)-Thr(ol) (SEQ ID NO: 1), or a derivative thereof, and at least one hexyloxycarbonyl moiety connected to at least one of the peptide's side chains or terminal amine groups. According to some embodiments, the at least one hexyloxycarbonyl moiety connected the amino terminus, a Lys side chain amine and/or a Trp side chain nitrogen, to form *DPhe-(Cys-Phe-*DTrp-*Lys-Thr-Cys)-Thr(ol), wherein * designates an optional hexyloxycarbonyl moiety connected to an amine group of the N-terminus or of an amino acid side chain, and (ol) designate an alcohol-carboxy terminus.

According to some embodiments, one hexyloxycarbonyl moiety is connected to the peptide's N-terminus.

According to some embodiments, the prodrug comprises 2 or 3 hexyloxycarbonyl moieties, wherein at least one is connected to a charged terminus or side chain of the somatostatin analog.

According to some specific embodiments, at least one permeability-enhancing moiety is connected to a charged terminus or side chain of the somatostatin analog and at least one additional permeability-enhancing moiety is connected to the amino group of a tryptophan (Trp) side chain of the somatostatin analog.

According to other embodiments, the prodrug comprises three hexyloxycarbonyl moieties connected to octreotide, one is connected to the N terminus of the peptide, one to the nitrogen atom of the side chain of the Trp residue, and one to the epsilon amine of the side chain of the Lysine (Lys) residue, to form 3-hexyloxycarbonyl octreotide (Octreotide-P) having the structure:

According to yet other embodiments, the prodrug comprises the head-to-tail cyclic N-methylated hexapeptide somatostatin denoted "Somato8" ("Peptide 8"), having the sequence (Pro-Phe-NMeDTrp-NMeLys-Thr-NMePhe) (SEQ ID NO: 8), wherein NMeDTrp is N-methyl D-Tryptophan, NMeLys is N-methyl Lysine and NMeF is N-methyl Phenylalanine.

According to some embodiments, the present invention provides a somatostatin prodrug comprising the cyclic somatostatin analog Somato8 (SEQ ID NO: 8) and at least one hexyloxycarbonyl moiety connected to the side chain of a Lys residue, a Trp residue, or both.

According to some specific embodiments, the prodrug is dihexyloxycarbonyl-Somato8 comprising two hexyloxycarbonyl moieties coupled to the somatostatin cyclic analog of SEQ ID NO: 8 to form the structure:

wherein one Hoc moiety is connected to the nitrogen of the amino group of the side-chain of the Trp residue and a second Hoc moiety is connected to the epsilon amine of the side chain of the Lys residue.

Hoc in all structures designates hexyloxycarbonyl residue having the structure:

According to other embodiments, the prodrug comprises a cyclic somatostatin analog comprising 1 or 2 substitutions, additions, deletions or combinations thereof, to the peptide of SEQ ID NO: 8.

According to some embodiments, the somatostatin prodrug comprises a backbone cyclic somatostatin analog in which at least one Nα-ω-functionalized derivative of an amino acid residue (building unit), is connected to another building unit, to the peptide's terminus or to an amino acid side chain to form a backbone cyclic bridge.

The backbone cyclized bridge of the somatostatin analog of the present invention may be formed by any type of chemical bond, including but not limited to: an amide bond, a thio-urea bond, an S—S bond, and a triazole click bond. The length of the bridge, defined by the type and number of the connecting groups, (typically methylene groups), can also vary.

Any backbone cyclic somatostatin analog known in the art, or a derivative thereof, may be used to construct the prodrugs of the present invention.

According to some specific embodiments, the backbone cyclic somatostatin analog is selected from the group consisting of:

PTR-3173 (Somatoprim) having the sequence GABA-Phe-Trp-DTrp-Lys-Thr-Phe-GlyC3-NH$_2$, (SEQ ID NO: 3) that is cyclized via a bridging group connected between the Nα-ω-functionalized derivative of a Glycine building unit (GlyC3) comprising a carboxyl reactive group and a three-carbon methylene spacer, and the N terminus of the gamma amino butyric acid (GABA) residue;

PTR-3046 having the sequence PheN2-Tyr-DTrp-Lys-Val-PheC3-Thr-NH$_2$ (SEQ ID NO: 9) that is cyclized via a bridging group connected between the Nα-ω-functionalized derivative of a Phenylalanine building unit (PheN2) comprising an amino reactive group and a two-carbon methylene spacer, and another Nα-ω-functionalized derivative of a Phenylalanine building unit (PheC3) comprising a carboxyl reactive group and a three-carbon methylene spacer; and PTR-3205 having the sequence PheC3-Cys-Phe-DTrp-Lys-Thr-Cys-Phe-PheN3-X (SEQ ID NO: 10), a bicyclic peptide comprising a disulfide bridge formed between the side chains of the two Cysteine (Cys) residues and a backbone cyclization bridge connecting the two building units PheC3 (comprising a carboxyl reactive group and a three-carbon methylene spacer) and PheN3 (comprising an amino reactive group and a three-carbon methylene spacer).

Additional backbone cyclized analogs, that can be used in prodrugs according to some embodiments of the present invention, are described in WO99/65508 and WO98/04583. According to some specific embodiments, the prodrug comprises a backbone cyclized somatostatin analog selected from the group consisting of:

```
PTR 3173
                                        SEQ ID NO: 3
GABA*-Phe-Trp-DTrp-Lys-Thr-Phe-GlyC3-X;

PTR 3046
                                        SEQ ID NO: 9
PheN2-Tyr-DTrp-Lys-Val-PheC3-Thr-X;

PTR 3205
                                       SEQ ID NO: 10
PheC3-Cys*-Phe-DTrp-Lys-Thr-Cys*-Phe-PheN3-X;

PTR 3171
                                       SEQ ID NO: 13
Phe*-Phe-Phe-DTrp-DLys-PheC2-X;

PTR 3113
                                       SEQ ID NO: 14
PheC1-Phe-Phe-DTrp-Lys-PheN2-X;

PTR 3123
                                       SEQ ID NO: 15
PheC1-Phe-Phe-DTrp-DLys-PheN2-X;

PTR 3209
                                       SEQ ID NO: 16
PheN2-Tyr-D2Nal-Lys-Val-GlyC2-Thr-X;
```

```
PTR 3183
                                          SEQ ID NO: 17
PheN2-Tyr-DTrp-Lys-Val-GlyC2-2Nal-X;

PTR 3185
                                          SEQ ID NO: 18
PheN2-Tyr-DTrp-Lys-Val-Val-GlyC2-X;

PTR 3201
                                          SEQ ID NO: 19
PheN2-Tyr-DTrp-Lys-Ser-2Nal-GlyC2-X;

PTR 3203
                                          SEQ ID NO: 20
PheN2-Phe-DTrp-Lys-Thr-2Nal-GlyC2-X;

PTR 3197
                                          SEQ ID NO: 21
Cys*-Phe-Trp-DTrp-Lys-Thr-Phe-GlyS2-X;

PTR 3207
                                          SEQ ID NO: 22
DPhe-Cys*-Phe-Trp-DTrp-Lys-Thr-Phe-GlyS2-X;

PTR 3229
                                          SEQ ID NO: 23
Galactose-Dab*-Phe-Trp-DTrp-Lys-Thr-Phe-GlyC3-X.
``` where X is —NH$_2$ or —OH and the bridging group extends between the two building units or: for PTR 3171 and PTR 3173, the asterisk denotes that the bridging group is connected between the Nα-ω-functionalized derivative of an amino acid and the N terminus of the peptide. For PTR 3197 and PTR 3207, the asterisk denotes that the bridging group is connected between the Nα-ω-functionalized derivative of an amino acid and the side chain of the Cys residue. PTR 3205 is a bicyclic compound in which one bridge connects the two building units (Phe-C3 and Phe-N3) and the second is a disulfide bridge formed between the two Cys residues.

The building units of the backbone cyclized somatostatin analogs are abbreviated by the three-letter code of the corresponding modified amino acid followed by the type of reactive group (N for amine, C for carboxyl), and an indication of the number of spacing methylene groups. For example, GlyC2 describes a modified Gly residue with a carboxyl reactive group and a two-carbon methylene spacer, and PheN3 designates a modified phenylalanine group with an amino reactive group and a three-carbon methylene spacer.

According to some embodiments, a prodrug of a somatostatin analog is provided wherein the somatostatin analog is a backbone cyclized analog in which the backbone cyclization bridge is formed by a bond selected from the group consisting of: an amide bond, a thiourea bond, a disulfide bond and a triazole click bond.

The carboxy terminus of any somatostatin peptide or peptide analog described above may be modified, for example by addition of an amide or alcohol group.

According to yet other embodiments, the somatostatin prodrug comprises the sequence NMeDTrp-NMeLys-Thr-NMePhe (SEQ ID NO: 11), wherein NMeDTrp is N-methyl D-Tryptophan, NMeLys is N-methyl Lysine and NMePhe is N-methyl-Phenylalanine.

According to some specific embodiments, the prodrug is Somato3M-P comprising three hexyloxycarbonyl moieties coupled to the backbone cyclic peptide Somato3M of the sequence Phe-Trp-NMeDTrp-NMeLys-Thr-NMePhe (SEQ ID NO: 12) to form the structure:

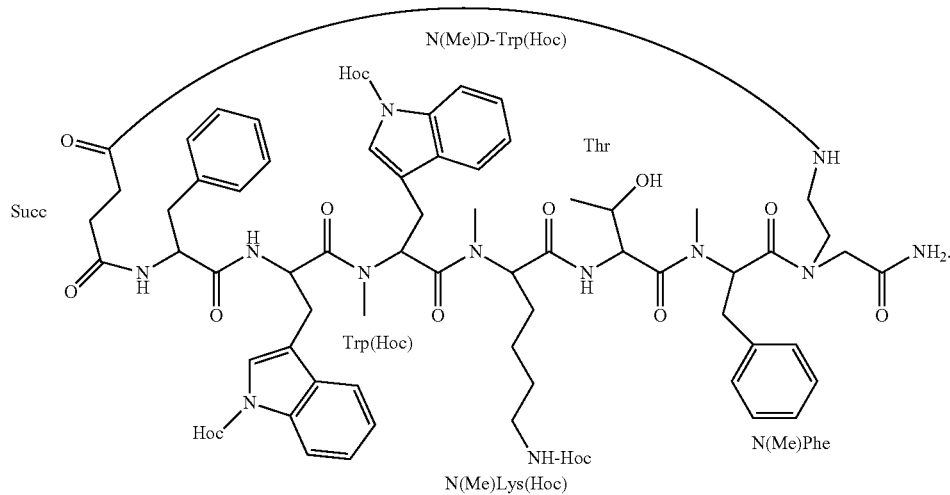

In some embodiments the somatostatin-based prodrug is having a net neutral charge.

In some embodiments the somatostatin-based prodrug is devoid of positively charged atoms.

In some embodiments the somatostatin-based prodrug is devoid of charged atoms.

According to some embodiments, the prodrug comprises the somatostatin peptide or peptide analog covalently linked to at least one oxycarbonyl moiety.

According to some embodiments, the prodrug comprises the somatostatin peptide or peptide analog covalently linked to at least one —CO$_2$R$^1$ moiety.

The term "oxycarbonyl" refers to the —CO$_2$— moiety. Similarly, the term "alkyl-oxycarbonyl" refers to the —CO$_2$— alkyl moiety.

According to some embodiments, the prodrug comprises at least one carbamate moiety.

According to some embodiments, the carbamate moiety is having a formula selected from the group consisting of:

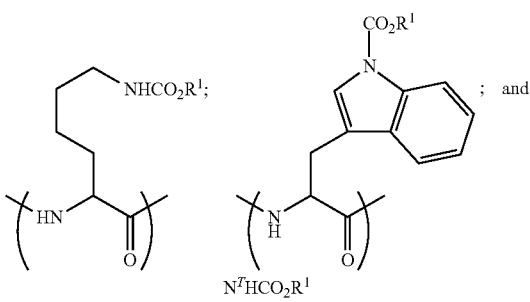

wherein $R^1$ is a primary alkyl;

According to some embodiments, $R^1$ is an alkyl group. According to some embodiments, $R^1$ is a primary alkyl group. According to some embodiments, $R^1$ is n-$C_6H_{13}$.

In some embodiments, $R^1$ is n-$C_{14}H_{29}$ (myristyl).

The term "primary alkyl group" as used herein, refers to an alkyl group, including substituted alkyl groups, unsubstituted alkyl groups, linear alkyl groups, and branched alkyl groups, so long that its first carbon atom is primary. With reference to $ClCO_2R^1$, $NCO_2R^1$, $NR^2CO_2R^1$, $CO_2R^1$ and similar groups, whereupon a primary alkyl is covalently connected to an oxygen atom, "primary alkyl group" comprises a methylene group bonded to the carbamate-sp$^3$ oxygen.

In some embodiments the primary alkyl is other than a primary benzyl or allyl.

In some embodiments $R^1$ is a primary alkyl group, with the proviso that $R^1$ is not a moiety selected from $CH_2$—Ar, $CH_2$—HetAr and $CH_2$—vinyl. Each possibility represents a separate embodiment. In some embodiments $R^1$ is a primary alkyl group, with the proviso that $R^1$ is not a primary benzyl group.

The term "benzyl" as used herein, refers to a —$CH_2$-aryl group.

The terms "aryl" and "Ar" as used herein, are interchangeable and refer to aromatic groups, such as phenyl, naphthyl and phenanthrenyl, which may optionally contain one or more substituents, such as alkyl, alkoxy, alkylthio, halo, hydroxy, amino and the like.

The terms "heteroaryl" and "HetAr" are interchangeable and refer to unsaturated rings of 5 to 14 atoms containing at least one O, N or S atoms. Heteroaryl may optionally be substituted with at least one substituent, including alkyl, aryl, cycloalkyl, alkoxy, halo amino and the like. Non limiting examples of heteroaryls include furyl, thienyl, pyrrolyl, indolyl and the like.

The term "vinyl" as used herein, refers to the ethene group —CH=$CH_2$, which may be substituted or unsubstituted. It may be combined with other groups to provide larger groups such as vinyl ether R—O—CH=CH—, where R is a may include but not limited to alkylene, alkenylene, arylene, and the like; vinyl ketone R(C=O)—CH=CH—, and the like.

In some embodiments $R^1$ is a primary $C_{3-40}$ alkyl. In some embodiments $R^1$ is a primary $C_{4-30}$ alkyl. In some embodiments $R^1$ is a primary $C_{3-20}$ alkyl. In some embodiments $R^1$ is a primary $C_{3-12}$ alkyl. In some embodiments $R^1$ is a primary $C_{4-20}$ alkyl. In some embodiments $R^1$ is a primary $C_{5-20}$ alkyl. It is to be understood by a person skilled in the art that "$C_{x-y}$" alkyl refers to an alkyl group as defined above, which has between x and y carbon atoms. For example $C_{5-20}$ alkyl may include, but not limited to, $C_5H_{11}$, $C_6H_{13}$, $C_{20}H_{41}$ and the like.

In some embodiments $R^1$ is a straight-chain alkyl. In some embodiments $R^1$ is an unsubstituted alkyl. In some embodiments $R^1$ is n-C—$H_{2n+1}$, wherein n is in the range of 3 to 15 or 5 to 12. In some embodiments $R^1$ is n-$C_6H_{13}$.

According to some embodiments, the oxycarbonyl moiety is a hexyloxycarbonyl (Hoc) moiety.

The invention provides, according to yet another aspect, a method of increasing the permeability and bioavailability of somatostatin analogs by masking at least one terminal or side-chain nitrogen atom of the somatostatin to form a somatostatin prodrug.

According to some embodiments, the side chain nitrogen atom is a tryptophan side chain nitrogen atom. According to some embodiments, the side chain nitrogen atom is a lysine side chain nitrogen atom. According to some embodiments, the side chain nitrogen atom is a N-terminus of the somatostatin.

According to yet another aspect, a method of producing cyclic somatostatin prodrugs is provided comprising reacting a somatostatin peptide or peptide analog with an alkyl haloformate to form a lipophilic carbamate somatostatin prodrug.

In some embodiments, there is provided a process for preparing a somatostatin-based prodrug, the process comprising:

(a) providing a somatostatin peptide or peptide analog; and (b) reacting said peptide with an alkyl haloformate, thereby forming the somatostatin-based prodrug.

The term "alkyl haloformate" refers to a compound having the formula X—$CO_2R$, wherein R is a primary alkyl and X is a halogen According to some embodiments, X is Cl.

According to some embodiments, the alkyl haloformate has the formula $XCO_2R^1$, wherein $R^1$ is as defined herein.

In some embodiments the somatostatin peptide or peptide analog of step (a) comprises at least one nucleophilic nitrogen atom.

In some embodiments the somatostatin peptide or peptide analog of step (a) comprises at least one side chain selected from tryptophan side chain and lysine side chain or, wherein said somatostatin-based prodrug comprises at least one carbamate moiety having the formula

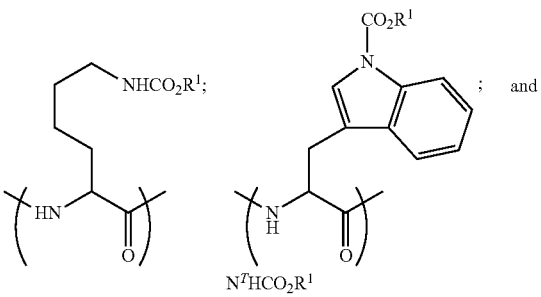

According to other embodiments, a step of cyclization of the somatostatin peptide or peptide analog is performed after step (b).

In some embodiments the somatostatin peptide or peptide analog of step (a) comprises at least one amino acid residue selected from the group consisting of lysine, tryptophan and combinations thereof.

In some embodiments step (b) is preformed in the presence of a base.

In some embodiments the base is triethylamine.

In some embodiments step (b) is preformed in acetonitrile solvent.

In some embodiments, somatostatin prodrugs as disclosed above are characterized by having a/at least one lipophilic $CO_2R^1$ group. Specifically, nucleophilic amine moiety or moieties within the starting somatostatin peptide or peptide analog of step (a) may be reactive towards chloroformates, forming a lipophilic N—$CO_2R^1$ residue(s), such as $CO_2R^1$ residue(s) residues linked to a tryptophan N atom. In some embodiments the nucleophilic amine moiety or moieties are derived from the amino terminus of the starting peptide, a nitrogen atom of tryptophan side chain, an amino moiety of a lysine side chain, and combinations thereof. In some embodiments at least one nucleophilic amine moiety is derived from a nitrogen atom selected from a nitrogen atom of a tryptophan side chain, a nitrogen atom of a lysine side chain and the N-terminus of the somatostatin.

Specifically, in some embodiments the somatostatin peptide or peptide analog of step (a) includes a terminal primary amine moiety, which is being protonated in physiological pH. In some embodiments reacting said peptide with an alkyl haloformate having the formula $XCO_2R^1$ results in a formation of an electronically neutral —$NHCO_2R^1$ group, thereby masking the charge of the peptide of step (a) and forming a somatostatin-based prodrug, which may resist protonation until after penetrating the intestinal membrane to the circulation or to the target tissue or cell.

It is further contemplated that inside cells, the prodrug would undergo an enzymatic reaction, e.g. with an esterase to form the somatostatin peptide in the circulation or in the target tissue or cell, where it is capable of executing its pharmacological effect. In some embodiments, the transformations presented above are relating to converting amines to carbamates. In some embodiments as the starting amine-containing peptides are basic, they may be protonated under physiological pH and thus, the transformations entail inhibiting the prodrug from acquiring positive charge.

In some embodiments the somatostatin-based prodrug is devoid of positively charged nitrogen atoms. In some embodiments the somatostatin-based prodrug is devoid of electrically charged nitrogen atoms. In some embodiments the somatostatin-based prodrug is having a net neutral charge. In some embodiments the somatostatin-based prodrug is devoid of positively charged atoms. In some embodiments the somatostatin-based prodrug is devoid of charged atoms. In some embodiment and as understood by a person skilled in the art, the reaction of step (b) may be facilitated in the presence of a base. Without wishing to be bound by any theory or mechanism of action, the peptide of step (a) may include protonated nitrogen atoms. Consequently, said protonated nitrogen atoms may show very low nucleophilicity and tendency to react with the alkyl chloroformate. As a result, an added base may deprotonate the protonated nitrogen atoms of the starting peptide and facilitate the reaction.

In some embodiment step (b) is preformed in the presence of a base. In some embodiment step (b) further comprises adding a base to the mixture of step (b).

In some embodiment the base is selected from an amine, a carbonate, a phosphate, a bicarbonate a hydroxide or a combination thereof. In some embodiment the base is an amine. In some embodiment the base is trimethylamine.

In some embodiment step (b) is performed in a solvent selected from the group consisting of acetonitrile, dimethyl formamide, dimethyl acetamide, dimethyl sulfoxide, ethanol, methanol and mixtures thereof. In some embodiment the solvent is acetonitrile.

In some embodiments, although the transformations presented above entail inhibiting the somatostatin prodrug from acquiring positive charge. it may also be desirable to inhibit negative charge(s) in peptides for enhancing the cellular permeability of the prodrugs. In some embodiments and typically negative charges on peptides may be derived from carboxylate groups, such as the starting peptide's carboxylic terminus, glutamic acid side chain(s) and/or aspartic acid side chain(s). It was found that such negative charges may be masked using $SOCl_2$ mediated esterification. It was further found that upon administration of the esterified prodrug, the ester groups may remain intact until reaching the target cell; while in the cell they undergo enzymatic de-esterification to their former state.

It is to be understood that the esterification may occur before or after the reaction of the starting peptide with the alkyl chloroformate.

In some embodiments the process further comprises a step of esterifying the somatostatin of step (a). In some embodiments the process further comprises a step of esterifying the somatostatin prodrug of step (b). In some embodiments the process further comprises a step of reacting the peptide-based prodrug with an alcohol in the presence of thionyl chloride. In some embodiments the process further comprises step (c) of reacting the peptide-based prodrug with an alcohol in the presence of thionyl chloride. In some embodiments step (a) further comprises reacting the peptide of step (a) with an alcohol in the presence of thionyl chloride.

According to some embodiments, the somatostatin prodrug is selected from the group consisting of: three-hexyloxycarbonyl-octreotide, dihexyloxycarbonyl-Somato8, and dihexyloxycarbonyl-Somato3M.

Pharmaceutical compositions comprising at least one somatostatin prodrug are provided according to another aspect of the present invention, as well as their use in treatment of diseases and disorders manageable with somatostatin analogs.

According to a specific embodiment, a pharmaceutical composition comprising at least one cyclic somatostatin prodrug described above is provided for use in treating a disease or disorder selected from the group consisting of: endocrine disease or disorder, metabolic disease or disorder, angiogenesis and cancer.

According to some embodiments, treatment comprises photodynamic therapy.

The pharmaceutical compositions of the present invention, comprising somatostatin prodrugs, are suitable for treatment, prevention or imaging of somatostatin receptor expressing or accumulating tumors. Such tumors, include but are not limited to pituitary, gastro-enteropancreatic, central nervous system, breast, prostatic (including advanced hormone-refractory prostate cancer), ovarian or colonic tumors, small cell lung cancer, malignant bowel obstruction, paragangliomas, kidney cancer, skin cancer, neuroblastomas, pheochromocytomas, medullary thyroid carcinomas, myelomas, lymphomas, Hodgkins and non-Hodgkins lymphomas, bone tumours and metastases thereof.

The pharmaceutical compositions are also suitable for prevention or treatment of autoimmune or inflammatory disorders, e.g. rheumatoid arthritis, Graves' disease or other inflammatory eye diseases.

The prodrugs of the present invention are also useful for the prevention or treatment of disorders with an etiology comprising or associated with excess growth hormone (GH) secretion and/or excess of insulin growth factor-1 (IGF-1), e.g. in the treatment of acromegaly as well as in the treatment of type I or type II diabetes mellitus, especially complications thereof, e.g. angiopathy, diabetic proliferative retinopathy, diabetic macular edema, nephropathy, neuropathy and dawn phenomenon, and other metabolic disorders related to insulin or glucagon release, e.g. obesity, e.g. morbid obesity or hypothalamic or hyperinsulinemic obesity. The somatostatin prodrugs are also useful in the treatment of enterocutaneous and pancreaticocutaneous fistula, irritable bowel syndrom, inflammatory diseases, e.g. Grave's Disease, inflammatory bowel disease, psoriasis or rheumatoid arthritis, polycystic kidney disease, dumping syndrom, watery diarrhea syndrom, AIDS-related diarrhea, chemotherapy-induced diarrhea, acute or chronic pancreatitis and gastrointestinal hormone secreting tumors (e.g. GEP tumors, for example vipomas, glucagonomas, insulinomas, carcinoids and the like), lymphocyte malignancies, e.g. lymphomas or leukemias, hepatocellular carcinoma as well as gastrointestinal bleeding, e.g. variceal oesophagial bleeding.

According to some embodiments, the metabolic disease is diabetes, including type 1 and type 2 diabetes.

According to some specific embodiments, the disease or disorder is selected from the group consisting of acromegaly and neuroendocrine tumors, e.g. carcinoid syndrome.

Pharmaceutical compositions for use in accordance with the present invention may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

According to some embodiments, the pharmaceutical compositions are formulated for oral administration.

According to other embodiments, the pharmaceutical compositions are formulated for parenteral administration.

According to some embodiments the formulation further comprises an excipient, carrier or diluent suitable for oral or parenteral administration. Suitable pharmaceutically acceptable excipients for use in this invention include those known to a person ordinarily skilled in the art such as diluents, fillers, binders, disintegrants and lubricants. Diluents may include but not limited to lactose, microcrystalline cellulose, dibasic calcium phosphate, mannitol, cellulose and the like. Binders may include but not limited to starches, alginates, gums, celluloses, vinyl polymers, sugars and the like. Lubricants may include but not limited to stearates such as magnesium stearate, talc, colloidal silicon dioxide and the like.

According to some embodiments, a pharmaceutical composition according to the present invention comprises at least one absorption enhancer, such as but not limited to, nanoparticles, piperine, curcumin and resveratrol.

According to some embodiments the pharmaceutical composition comprises a delivery system selected from the group consisting of: a Pro-NanoLipospheres (PNL) composition, an Advanced PNL and a self-nano emulsifying drug delivery system (SNEDDS).

According to other embodiments, a composition comprising a somatostatin prodrug according to the invention comprises at least one agent that reduce intra-enterocyte metabolism by CYP3A4 or reduce P-gp efflux activity. According to some specific embodiments, the agent that reduce Pg-p efflux is verapamil.

The pharmaceutical compositions and the uses of the present invention may comprise, according to some embodiments, at least one additional active agent.

The present invention provides, according to another aspect, a method of prevention, alleviation or treatment of a disease or disorder amendable with somatostatin or somatostatin analog, comprising administering to a subject in need thereof, a pharmaceutically active amount of somatostatin prodrug according to the invention.

According to certain embodiments the disease or disorder is an endocrine disease or disorder, metabolic disease or disorder, angiogenesis or cancer.

Administering of a somatostatin prodrug or a pharmaceutical composition comprising the somatostatin prodrug according to the present invention may be orally or parenterally.

According to some embodiments the administration route is selected from the group consisting of: orally, topically, intranasally, subcutaneously, intramuscularly, intravenously, intra-arterially, intraarticulary, or intralesionally.

According to some embodiments, treatment comprises photodynamic therapy using the somatostatin prodrugs of the present invention.

The somatostatin prodrugs of the present invention may be administered alone or in combination with other therapeutic agents or additional therapies. Such therapies include but are not limited to radiotherapy, surgery, immunotherapy and combinations thereof.

According to some embodiments, the method comprises administering a somatostatin prodrug and at least one absorption enhancer and/or at least one agent that reduce intra-enterocyte metabolism by CYP3A4 or reduce P-gp efflux activity. According to some specific embodiments, the agent that reduce Pg-p efflux is verapamil.

According to yet another aspect, the somatostatin prodrugs according to the invention are used for diagnosis and imaging. Any disease or disorder that may be diagnosed with somatostatin analog may be also diagnosed with the prodrugs of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURE

FIG. 1 is a bar chart describing the results of permeability transport studies (A to B—apical to basolateral, and B to A—basolateral to apical), of the prodrug octreotide-P (denoted OCT-Hoc-2), in comparison to the control molecules atenolol and metoprolol.

DETAILED DESCRIPTION OF THE INVENTION

In the search for bioavailable somatostatin analogs, lipophilic carbamate prodrug molecules have been produced and showed improved permeability.

The present invention provides methods that modify the active somatostatin peptide structure and enable transcellular absorption pathway from the intestine lumen to the blood circulation. The methods comprise converting charged somatostatin peptides into their lipophilic carbamate prodrugs, thereby, shifting the mechanism of intestinal permeability of the charged drug peptides from para-cellular to trans-cellular pathway of their lipophilic prodrugs. This is done by reducing the polarity and charge of the peptide, and thus improving its membrane permeability and oral bioavailability. The prodrug enhanced intestinal permeability allows its absorption to the blood stream where esterases remove the pro-moiety to regenerate the parent active somatostatin peptide.

The present disclosure is also directed to various synthetic processes for the preparation of somatostatin prodrugs. Said prodrugs are generally characterized by two main chemical features: (a) reduction or omission of electrically charged atoms in the peptide sequence, e.g. through charge masking of charged amino acid residues and terminal amino and carboxylate moieties; and (b) improved lipophilicity provided through introduction of lipophilic groups. A further feature presented by somatostatin-based prodrugs prepared according to some embodiments of the present processes is their lability in the presence of specific enzymes, which transform the somatostatin prodrugs into charged biologically active somatostatin compounds.

A common feature to the processes disclosed herein, is the modification of amino acids and/or amino acid residues to their modified counterparts, which include carbamate(s) of primary alcohols. In some embodiments, amino side chains having amine moieties are transformed into carbamates having —$NCO_2R$ groups; whereas amino side chains having carboxylate moieties are transformed into esters having —$CO_2R$ groups. In some embodiments, since the esters and amines are of primary alcohols, R is primary, i.e. the first group covalently bonded to the carbonyl's α-$sp^3$ oxygen is a methylene group.

The present invention is based in part on the finding that unlike tertiary carbamates, primary carbamates do not transform into their corresponding amines or ammonium ions until after penetrating the intestine membrane and reaching the circulation, the target tissue or the target cell, where specific proteases are present. Without wishing to be bound by any theory or mechanism of action, the commonly used tertiary carbamates (e.g. compound having the tert-butyloxycarbonyl-amino, N—$CO_2CMe_3$ moiety, N—BOC) undergo O—$CMe_3$ bond cleavage in gastrointestinal pH. In contrast, primary alkyl carbamates, of the prodrugs of the present invention, are relatively stable until after penetrating through the intestine membrane and reach the circulation, the lymphatic system, and/or the blood stream. Therefore, tertiary carbamates undergo O—$CMe_3$ bond cleavage before reaching the circulation or target tissue, to form the corresponding carbamic acids (having a —NH—$CO_2H$ group), which undergo spontaneous decarboxylation to form amines. Said amines are then being protonated under gastrointestinal pH to form charged peptides which undergo degradation before reaching the cells. On the other hand, it was surprisingly found that a similar sequence of reactions, occurs with primary carbamates only in the presence of specific esterases, which target and break the O—$CH_2$ or the carbonyl-$OCH_2$ bond in the blood stream, lymphatic system, target tissue or inside the target cell.

Example prodrugs according to the present invention have been produced by chemical synthesis and selected based on the results achieved in permeability assay screening. The permeability assays include evaluation of intestinal permeability and metabolic stability in relevant in vitro models. Evaluation of pharmacokinetics following oral administration is tested in vivo in freely moving rats. Comparing the activity of the somatostatin peptide drugs with their prodrugs following oral administration is performed by administration intravenously or orally.

The somatostatin prodrugs of the present invention are used to substitute somatostatin peptides and derivatives in therapeutic application amendable with this drug, for example in treatment of cancer and metabolic diseases. The conversion of the somatostatin treatment from parenteral mode of administration to much more convenient oral intake will significantly increase patient compliance and would be preferred by clinical team.

Somatostatin, both in its natural and synthetic derivative forms is ultimately used as a cyclic peptide and has many derivatives and analogs that are all characterized by having cyclic structure. Cyclization of peptides has been shown to be a useful approach in developing diagnostically and therapeutically useful peptidic and peptidomimetic agents. Cyclization of peptides reduces the conformational freedom of these flexible, linear molecules, and often results in higher receptor binding affinities by reducing unfavorable entropic effects. Because of the more constrained structural framework, these agents are more selective in their affinity to specific receptor cavities. By the same reasoning, structurally constrained cyclic peptides confer greater stability against the action of proteolytic enzymes.

Methods for cyclization can be classified into cyclization by the formation of the amide bond between the N-terminal and the C-terminal amino acid residues, and cyclizations involving the side chains of individual amino acids. The latter method includes the formation of disulfide bridges between two w-thio amino acid residues (cysteine, homocysteine), the formation of lactam bridges between glutamic/aspartic acid and lysine residues, the formation of lactone or thiolactone bridges between amino acid residues containing carboxyl, hydroxyl or mercapto functional groups, the formation of thioether or ether bridges between the amino acids containing hydroxyl or mercapto functional groups and other special methods. Lambert, et al., reviewed variety of peptide cyclization methodologies (J. Chem. Soc. Perkin Trans., 2001, 1:471-484).

Some of the parent somatostatin analogs used to produce the prodrug of the present invention are backbone cyclized peptides. Backbone cyclization is a general method by which conformational constraint is imposed on peptides. In backbone cyclization, atoms in the peptide backbone (N and/or C) are interconnected covalently to form a ring. Backbone cyclized analogs are peptide analogs cyclized via bridging groups attached to the alpha nitrogens or alpha carbonyl of amino acids. In general, the procedures utilized to construct such peptide analogs from their building units rely on the known principles of peptide synthesis; most conveniently, the procedures can be performed according to the known principles of solid phase peptide synthesis. During solid phase synthesis of a backbone cyclized peptide the protected building unit is coupled to the N-terminus of the peptide chain or to the peptide resin in a similar procedure to the coupling of other amino acids. After completion of the peptide assembly, the protective group is removed from the building unit's functional group and the cyclization is accomplished by coupling the building unit's functional group and a second functional group selected from a second building unit, a side chain of an amino acid residue of the peptide sequence, and an N-terminal amino acid residue.

As used herein the term "backbone cyclic peptide" or "backbone cyclic analog" refers to a sequence of amino acid residues wherein at least one nitrogen or carbon of the peptide backbone is joined to a moiety selected from another such nitrogen or carbon, to a side chain or to one of the termini of the peptide. According to specific embodiment of the present invention the peptide sequence is of 5 to 15 amino acids that incorporates at least one building unit, said building unit containing one nitrogen atom of the peptide backbone connected to a bridging group comprising an amide, thioether, thioester, disulfide, urea, carbamate, or sulfonamide, wherein at least one building unit is connected via said bridging group to form a cyclic structure with a moiety selected from the group consisting of a second building unit, the side chain of an amino acid residue of the sequence or a terminal amino acid residue. Furthermore, one or more of the peptide bonds of the sequence may be reduced or substituted by a non-peptidic linkage.

A "building unit" (BU) indicates a $N^\alpha$-ω-functionalized or an $C^\alpha$-ω-functionalized derivative of amino acids. Use of such building units permits different length and type of linkers and different types of moieties to be attached to the scaffold. This enables flexible design and easiness of production using conventional and modified solid-phase peptide synthesis methods known in the art.

The $N^\alpha$-ω-functionalized derivative of amino acids preferably have the following structure:

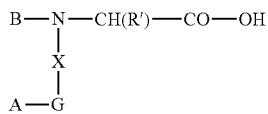

wherein X is a spacer group selected from the group consisting of alkylene, substituted alkylene, arylene, cycloalkylene and substituted cycloalkylene; R' is an amino acid side chain, optionally bound with a specific protecting group; B is a protecting group selected from the group consisting of alkyloxy, substituted alkyloxy, or aryl carbonyls; and G is a functional group selected from the group consisting of amines, thiols, alcohols, carboxylic acids and esters, aldehydes, alcohols and alkyl halides; and A is a specific protecting group of G.

According to some embodiments, the building units are ω-functionalized amino acid derivatives wherein X is alkylene; G is a thiol group, an amino group or a carboxyl group; and R' is the side chain of an amino acid. According to some embodiments R' is protected with a specific protecting group.

According to some specific embodiments, G is an amino group, a carboxyl group, or a thiol group.

The methodology for producing the building units is described for example in WO95/33765 and WO98/04583 and in U.S. Pat. Nos. 5,770,687 and 5,883,293.

The building units are abbreviated by the three-letter code of the corresponding modified amino acid followed by the type of reactive group (N for amine, C for carboxyl), and an indication of the number of spacing methylene groups. For example, GlyC2 describes a modified Gly residue with a carboxyl reactive group and a two-carbon methylene spacer, and PheN3 designates a modified phenylalanine group with an amino reactive group and a three carbon methylene spacer.

In general, the procedures utilized to construct backbone cyclic molecules and their building units rely on the known principles of peptide synthesis and peptidomimetic synthesis; most conveniently, the procedures can be performed according to the known principles of solid phase peptide synthesis. Some of the methods used for producing $N^\alpha$ω building units and for their incorporation into peptidic chain are disclosed in U.S. Pat. Nos. 5,811,392; 5,874,529; 5,883,293; 6,051,554; 6,117,974; 6,265,375, 6,355613, 6,407059, 6,512,092 and international applications WO95/33765; WO97/09344; WO98/04583; WO99/31121; WO99/65508; WO00/02898; WO00/65467 and WO02/062819.

The production and activity of some of the backbone cyclic somatostatin peptide analogs, used in the present invention for preparing the prodrugs where disclosed previously, for example in U.S. Pat. No. 5,770,687 and WO99/65508.

As used herein "peptide" indicates a sequence of amino acids linked by peptide bonds. Functional derivatives of the peptides of the invention covers derivatives which may be prepared from the functional groups which occur as side chains on the residues or the N- or C-terminal groups, by means known in the art, and are included in the invention. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl groups (for example those of seryl or threonyl residues) formed by reaction with acyl moieties. Salts of the peptides of the invention contemplated by the invention are organic and inorganic salts.

The compounds herein disclosed may have asymmetric centers. All chiral, diastereomeric, and racemic forms are included in the present invention. Many geometric isomers of double bonds and the like can also be present in the compounds disclosed herein, and all such stable isomers are contemplated in the present invention.

The term "amino acid" refers to compounds, which have an amino group and a carboxylic acid group, preferably in a 1,2-1,3-, or 1,4-substitution pattern on a carbon backbone. α-Amino acids are most preferred, and include the 20 natural amino acids (which are L-amino acids except for glycine) which are found in proteins, the corresponding D-amino acids, the corresponding N-methyl amino acids, side chain modified amino acids, the biosynthetically available amino acids which are not found in proteins (e.g., 4-hydroxy-proline, 5-hydroxy-lysine, citrulline, ornithine, canavanine, djenkolic acid, β-cyanolanine), and synthetically derived α-amino acids, such as amino-isobutyric acid, norleucine, norvaline, homocysteine and homoserine. β-Alanine and γ-amino butyric acid are examples of 1,3 and 1,4-amino acids, respectively, and many others are well known to the art.

Some of the amino acids used in this invention are those which are available commercially or are available by routine synthetic methods. Certain residues may require special methods for incorporation into the peptide, and either sequential, divergent or convergent synthetic approaches to the peptide sequence are useful in this invention. Natural coded amino acids and their derivatives are represented by three-letter codes according to IUPAC conventions. When there is no indication, the L isomer was used. The D isomers are indicated by "D" or "(D)" before the residue abbreviation or by using the lower case of the amino acid code.

Conservative substitution of amino acids as known to those skilled in the art are within the scope of the present invention. Conservative amino acid substitutions includes replacement of one amino acid with another having the same type of functional group or side chain e.g. aliphatic, aromatic, positively charged, negatively charged. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K), Histidine (H);
5) Isoleucine (I), Leucine (L), Methionine (M), Valine (V); and
6) Phenylalanine (F), Tyrosine (Y), Tryptophan (W).

The terms "N-methylation" or "NMe" are used herein interchangeably and refer to a form of alkylation wherein a methyl group, CH3, replaces the hydrogen atom of the NH moiety in the backbone amide NHs of residues within the peptides. The terms refer to a peptide having at least one N-methylated amino acid.

Click reactions occur in one pot, are not disturbed by water, generate minimal and inoffensive byproducts, and are "spring-loaded" characterized by a high thermodynamic driving force that drives it quickly and irreversibly to high yield of a single reaction product, with high reaction specificity (in some cases, with both regio- and stereo-specificity). Click reactions are particularly suitable to the problem of isolating and targeting molecules in complex biological environments. In such environments, products accordingly need to be physiologically stable and any byproducts need to be non-toxic (for in vivo systems).

Prodrugs

The prodrugs disclosed in the present invention are generally characterized by two main chemical features: (a) reduction or omission of electrically charged atoms in the peptide skeleton, e.g. through charge masking of charged amino acid residues and terminal amino and carboxylate moieties; and (b) improved lipophilicity provided through introduction of lipophilic groups. A further feature presented by peptide-based prodrugs prepared according to some embodiments of the present processes is their lability in the presence of cellular enzymes, which transform the prodrugs into charged biologically active peptide drugs.

The term "prodrug" as used herein refers to an inactive or relatively less active form of an active agent that becomes active through one or more metabolic processes in a subject.

The term "masking moiety" as used herein refers to a moiety that reduce the net electric charge of the peptide such as Hexyloxycarbonyl (Hoc).

The term "carbamate" as used herein alone or in combination refers to a chemical group or moiety represented by the general structure —N(CO)O—. Carbamate esters may have alkyl or aryl groups substituted on the oxygen.

A common feature to processes for producing the prodrugs disclosed herein, according to some embodiments, is the modification of amino acids and/or amino acid residues to their modified counterparts, which include an ester(s) and/or carbamate(s) of primary alcohols. In some embodiments and generally, amino side chains having amine moieties are transformed into carbamates having —NHCO$_2$R moieties; whereas amino side chains having carboxylate moieties are transformed into esters having —CO$_2$R moieties. In some embodiments, since the esters and amines are of primary alcohols, R is primary, i.e. the first group covalently bonded to the carbonyl's sp$^3$ oxygen is a methylene group.

It is shown now that unlike tertiary carbamates, primary carbamates do not transform into their corresponding amines or ammonium ions until after penetrating the circulation or target tissue. Without wishing to be bound by any theory or mechanism of action, the commonly used tertiary carbamates (e.g. compound having the tert-nutyloxycarbonyl-amino, NH—CO$_2$CMe$_3$ moiety) undergo O—CMe$_3$ bond cleavage in physiological pH. In contrast, primary alkyl carbamates are relatively stable until after penetrating the circulation or target cells. Therefore, tertiary carbamates undergo O—CMe$_3$ bond cleavage before reaching the cell (typically in the intestines), to form carbamic acids (NH—CO$_2$H), which undergo spontaneous decarboxylation to form amines, which are then being protonated to form a charged peptide, which is unable to penetrate the intestinal membrane or undergoes degradation before reaching the circulation or cells. On the other hand, it was surprisingly found that a similar sequence of reactions, occurs with primary carbamates only after penetrating the intestine into blood stream or lymphatic system, where the peptide-based drug is carried as active form to the target tissue. It is hypothesized that the difference stems from the high tendency of tertiary carbamates to form tertiary carbocations under acidic conditions, while primary carbamates tend to cleave in the presence of inter-cellular esterases, which break the O—CH$_2$ bond in vivo.

In some embodiments, some the processes disclosed herein are distinctive in the stage in which the modification occurs. Whereas in some of the processes a modification is performed on an amino acid prior to its incorporation to the prodrug in a peptide synthesis; in some processes the modification is performed on an amino acid residue during the peptide synthesis; and in some of the processes the modification is preformed after the completion of the peptide synthesis.

As used herein the term "salts" refers to both salts of carboxyl groups and to acid addition salts of amino or guanido groups of the peptide molecule, if available. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and/or mineralization of calcium minerals.

The peptides of the present invention may be produced by any synthetic method known in the art. In some circumstances, a recombinant method can be used to synthesize a somatostatin peptide comprising naturally coded amino acids. Synthetic methods include exclusive solid phase synthesis, partial solid phase synthesis, fragment condensation, or classical solution synthesis. In some embodiments, synthetic peptides are purified by preparative high-performance liquid chromatography. The conjugation of the lipophilic moiety may be performed, according to some embodiments, during synthesis of the peptide or according to other embodiments after the synthesis, cleavage and purification of the peptide.

"Permeability" refers to the ability of an agent or substance to penetrate, pervade, or diffuse through a barrier, membrane, or a skin layer. A "cell permeability moiety", a "permeability enhancing moiety" or a "cell-penetration moiety" refers to any molecule known in the art which is able to facilitate or enhance penetration of molecules through membranes. Non-limitative examples include: hydrophobic moieties such as lipids, fatty acids, steroids and bulky aromatic or aliphatic compounds; moieties which may have cell-membrane receptors or carriers, such as steroids, vitamins and sugars, natural and non-natural amino acids and transporter peptides.

Pharmacology

The compounds of the present invention can be formulated into various pharmaceutical forms for purposes of administration. Pharmaceutical composition of interest may comprise at least one additive selected from a disintegrating agent, binder, flavoring agent, preservative, colorant and a mixture thereof, as detailed for example in "Handbook of Pharmaceutical Excipients"; Ed. A. H. Kibbe, 3rd Ed., American Pharmaceutical Association, USA.

For example, a compound of the invention, or its salt form or a stereochemically isomeric form, can be combined with a pharmaceutically acceptable carrier. Such a carrier can depend on the route of administration, such as oral, rectal, percutaneous or parenteral injection.

A "carrier" as used herein refers to a non-toxic solid, semisolid or liquid filler, diluent, vehicle, excipient, solubilizing agent, encapsulating material or formulation auxiliary of any conventional type, and encompasses all of the components of the composition other than the active pharmaceutical ingredient. The carrier may contain additional agents such as wetting or emulsifying agents, or pH buffering agents. Other materials such as anti-oxidants, humectants, viscosity stabilizers, and similar agents may be added as necessary.

For example, in preparing the compositions in oral dosage form, media such as water, glycols, oils, alcohols can be used in liquid preparations such as suspensions, syrups, elixirs, and solutions. Alternatively, solid carriers such as starches, sugars, kaolin, lubricants, binders, disintegrating agents can be used, for example, in powders, pills, capsules or tablets.

The pharmaceutically acceptable excipient(s) useful in the composition of the present invention are selected from but not limited to a group of excipients generally known to persons skilled in the art e.g. diluents such as lactose (Pharmatose DCL 21), starch, mannitol, sorbitol, dextrose, microcrystalline cellulose, dibasic calcium phosphate, sucrose-based diluents, confectioner's sugar, monobasic calcium sulfate monohydrate, calcium sulfate dihydrate, calcium lactate trihydrate, dextrates, inositol, hydrolyzed cereal solids, amylose, powdered cellulose, calcium carbonate, glycine, and bentonite; disintegrants; binders; fillers; bulking agent; organic acid(s); colorants; stabilizers; preservatives; lubricants; glidants/antiadherants; chelating agents; vehicles; bulking agents; stabilizers; preservatives; hydrophilic polymers; solubility enhancing agents such as glycerin, various grades of polyethylene oxides, transcutol and glycofiirol; tonicity adjusting agents; pH adjusting agents; antioxidants; osmotic agents; chelating agents; viscosifying agents; wetting agents; emulsifying agents; acids; sugar alcohol; reducing sugars; non-reducing sugars and the like, used either alone or in combination thereof. The disintegrants useful in the present invention include but not limited to starch or its derivatives, partially pregelatinized maize starch (Starch 1500°), croscarmellose sodium, sodium starch glycollate, clays, celluloses, alginates, pregelatinized corn starch, crospovidone, gums and the like used either alone or in combination thereof. The lubricants useful in the present invention include but not limited to talc, magnesium stearate, calcium stearate, sodium stearate, stearic acid, hydrogenated vegetable oil, glyceryl behenate, glyceryl behapate, waxes, Stearowet, boric acid, sodium benzoate, sodium acetate, sodium chloride, DL-leucine, polyethylene glycols, sodium oleate, sodium lauryl sulfate, magnesium lauryl sulfate and the like used either alone or in combination thereof. The anti-adherents or glidants useful in the present invention are selected from but not limited to a group comprising talc, corn starch, DL-leucine, sodium lauryl sulfate, and magnesium, calcium and sodium stearates, and the like or mixtures thereof. In another embodiment of the present invention, the compositions may additionally comprise an antimicrobial preservative such as benzyl alcohol. In an embodiment of the present invention, the composition may additionally comprise a conventionally known antioxidant such as ascorbyl palmitate, butylhydroxyanisole, butylhydroxytoluene, propyl gallate and/or tocopherol. In another embodiment, the dosage form of the present invention additionally comprises at least one wetting agent(s) such as a surfactant selected from a group comprising anionic surfactants, cationic surfactants, non-ionic surfactants, zwitterionic surfactants, or mixtures thereof. The wetting agents are selected from but not limited to a group comprising oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate and the like, or mixtures thereof. In yet another embodiment, the dosage form of the present invention additionally comprises at least one complexing agent such as cyclodextrin selected from a group comprising but not limited to alpha-cyclodextrin, beta-cyclodextrin, betahydroxy-cyclodextrin, gamma-cyclodextrin, and hydroxypropyl beta-cyclodextrin, or the like. In yet another embodiment, the dosage form of the present invention additionally comprises of lipid(s) selected from but not limited to glyceryl behenate such as Compritol® ATO888, Compritol® ATO 5, and the like; hydrogenated vegetable oil such as hydrogenated castor oil e.g. Lubritab®; glyceryl palmitostearate such as Precirol® ATO 5 and the like, or mixtures thereof used either alone or in combination thereof. It will be appreciated that any given excipient may serve more than one function in the compositions according to the present invention.

For parenteral compositions, the carrier can comprise sterile water. Other ingredients may be included to aid in solubility. Injectable solutions can be prepared where the carrier includes a saline solution, glucose solution or mixture of both.

Injectable suspensions can also be prepared. In addition, solid preparations that are converted to liquid form shortly before use can be made. For percutaneous administration, the carrier can include a penetration enhancing agent or a wetting agent.

It can be advantageous to formulate the compositions of the invention in dosage unit form for ease of administration and uniformity of dosage. "Dosage unit form" refers to physically discrete units suitable as unitary dosages, each unit containing a pre-determined quantity of active ingredient calculated to produce the desired therapeutic effect in association with the chosen carrier.

Apart from other considerations, the fact that the active ingredients of the invention are peptides, peptide analogs or peptidomimetics, dictates that the formulation be suitable for delivery of these types of compounds. Although in general peptides are less suitable for oral administration due to susceptibility to digestion by gastric acids or intestinal enzymes. According to the present invention, novel methods of are being used, in order to synthesize metabolically stable and oral bioavailable somatostatin prodrugs. The preferred route of administration of peptides of the invention is oral administration.

Other routes of administration include but are not limited to intra-articular, intravenous, intramuscular, subcutaneous, intradermal, topical or intrathecal.

Pharmaceutical compositions according to the present invention may also comprise at least one absorption enhancer, such as but not limited to, nanoparticles, piperine, curcumin and resveratrol.

In addition, or alternatively, the compositions and administration methods of the present invention may include agents and formulations that reduce intra-enterocyte metabolism by CYP3A4 and/or reduce P-gp efflux activity, for example, the Pg-p inhibitor verapamil.

Suitable delivery systems for the prodrugs of the present invention, are for example Pro-NanoLipospheres (PNL) and Advanced PNL disclosed in WO2013/208254 [32], and the self-nano-emulsifying drug delivery system (SNEDDS) [33].

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example polyethylene glycol are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

For buccal administration, the compositions may take the form of tablets or lozenges formulated in conventional manner.

For administration by inhalation, the variants for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art (Pillai et al., 2001, Curr. Opin. Chem. Biol. 5, 447). Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of a compound effective to prevent, alleviate or ameliorate symptoms of a disease of the subject being treated. Determination of a therapeutically effective amount is well within the capability of those skilled in the art.

Toxicity and therapeutic efficacy of the peptides described herein can be determined by standard pharmaceutical procedures in cell cultures or experimental animals, e.g., by determining the IC50 (the concentration which provides 50% inhibition) and the LD50 (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (e.g. Fingl, et al., 1975, in "The Pharmacological Basis of Therapeutics", Ch. 1 p. 1).

Those skilled in the art of treatment can determine the effective daily amount, optionally based on the known amount of the parent somatostatin compound in use. The precise dosage and frequency of administration depends on the particular compound of the invention being used, as well as the particular condition being treated, the severity of the condition, the age, weight, and general physical condition of the subject being treated, as well as other medication being taken by the subject, as is well known to those skilled in the art. It is also known that the effective daily amount can be lowered or increased depending on the response of the subject or the evaluation of the prescribing physician. Thus, the ranges mentioned above are only guidelines and are not intended to limit the scope of the use of the invention.

The combination of a compound of the invention with another agent used for treatment can be used. Such combination can be used simultaneously, sequentially or separately.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

General Procedures

Chromatography

Semi-preparative reversed phase HPLC was performed using Waters instruments: Waters 2545 (Binary Gradient Module), Waters SFO (System Fluidics Organizer), Waters 2996 (Photodiode Array Detector), Waters 2767 (Sample Manager). A C18-column: Reprosil 100 C18, 5 μm, 150×30 mm was used. The Semi-preparative RP-HPLC columns were operated with a flow rate of 40 mL/min with a linear gradient (20 min) of $H_2O$ (0.1% v/v trifluoroacetic acid (TFA)) and acetonitrile (0.1% v/v TFA). Analytical HESI-HPLC-MS (heated electrospray ionization mass spectrometry) was performed on an LCQ Fleet (Thermo Scientific) with a connected UltiMate 3000 UHPLC focused (Dionex) on C18-columns: 51: Hypersil Gold aQ 175 Å, 3 μm, 150×2.1 mm (for 8 or 20 minutes measurements); S2: Accucore C18, 80 Å, 2.6 μm, 50×2.1 mm (for 5 minute measurements) (Thermo Scientific). Linear gradients (5%-95% acetonitrile content) with $H_2O$ (0.1% v/v formic acid) and acetonitrile (0.1% v/v formic acid) as eluents were used.

Permeability Studies

Colorectal adenocarcinoma 2 (Caco-2) cells (ATTC) were grown in 75 $cm^2$ flasks with approximately $0.5 \times 10^6$ cells/flask (Thermo-Fischer) at 37° C. in a 5% $CO_2$ atmosphere and at relative humidity of 95%. The culture growth medium consisted of DMEM supplemented with 10% heat-inactivated FBS, 1% MEM-NEAA, 2 mM l-glutamine, 1 mM sodium pyruvate, 50,000 units Penicillin G Sodium and 50 mg Streptomycin Sulfate (Biological Industries). The medium was replaced every other day.

Caco-2 cells (passage 55-60) were seeded at density of $25 \times 10^5$ cells/$cm^2$ on untreated culture inserts of polycarbonate membrane with 0.4 μm pores and surface area of 1.1 $cm^2$. Culture inserts containing Caco-2 monolayer were placed in 12 mm transwell plates (Corning). Culture medium was replaced every other day. Transepithelial Electrical Resistance (TEER) values were measured by Millicell ERS-2 System (Millipore) a week after seeding up to experiment day (21-23 days) to ensure proliferation and differentiation of the cells. When the cells were fully differentiated and TEER values became stable (200-500 $\Omega \cdot cm^2$). The TEER values were compared to control inserts containing only the medium.

In vitro permeability studies using Caco-2 cells were initiated by replacing the medium from both sides by apical (600 μl) and basolateral (1500 μl) buffers, both warmed to 37° C. The cells were incubated with the buffers solutions for 30 min at 37° C. on a shaker (100 cycles/min). The apical buffer was replaced by apical buffer containing 10 μg/ml of the somatostatin peptide or the somatostatin prodrug. 50 μl samples were taken from the apical side immediately at the beginning of the experiment, resulting in 550 μl apical volume during the experiment. Samples of 200 μl at fixed time points (20, 40, 60, 80, 100, 120 and 150 min) from the basolateral side and replaced with the same volume of fresh basolateral buffer to maintain a constant volume. The experiment included two control compounds, atenolol and metoprolol, as paracellular and transcellular permeability markers respectively.

Permeability Coefficient (Papp) for each compound was calculated from the linear plot of drug accumulated versus time, using the following equation:

$$Papp = \frac{dq/dt}{C_0 \times A}$$

Where dq/dt is steady state appearance rate of the compound on the receiver side, $C_0$ is the initial concentration of the drug on the donor side, and A is the exposed tissue surface area (1.1 $cm^2$).

In Vivo Studies

Somatostatin peptides, analogs and prodrugs according to the present invention are evaluated in vivo using methods know in the art for assessing the activity of somatostatin. For example, the in vivo effects on the release of glucagon, insulin and growth hormone may be evaluated according to the method described in WO99/65508.

In a tumor growth model, female nude mice weighing 19-22 g are kept in groups of 5 animals and have free access to drinking water and a pathogen-free rodent diet. Subcutaneous tumors are initiated from cultured AR42J cells. Treatment commences 2-4 days following inoculation of the tumor cells. The tested compounds are administered parenterally or orally. The size of the tumors is determined with a caliper. For statistical calculations Student's t-test is applied.

EXAMPLES

Example 1. Preparation of Octreotide Prodrug

The prodrug three hexyloxycarbonyl-octreotide (Octreotide-P) was synthesized from octreotide using the synthetic pathway shown in Scheme 1:

Scheme 1. Preparation of tri-hexyloxycarbonyl octreotide (Octreotide-P) from octreotide.
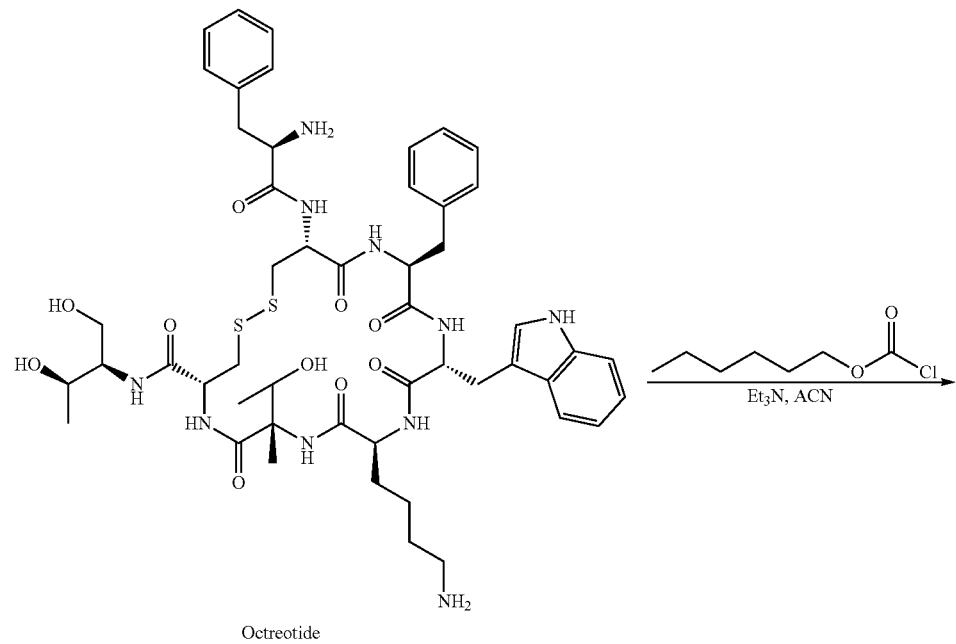
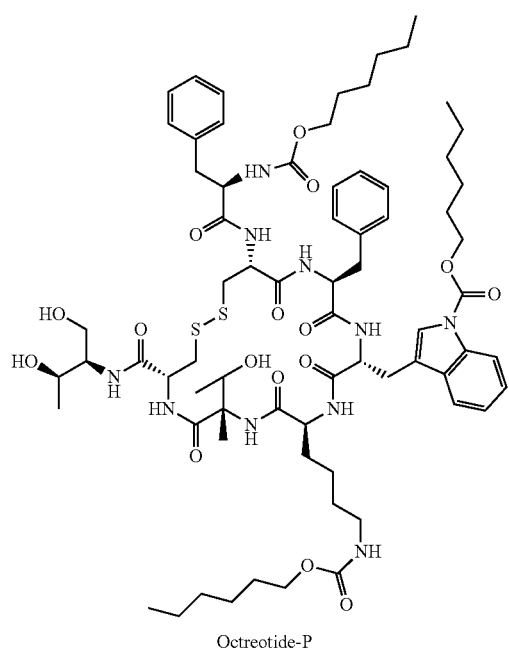

Example 2. Synthesis of Somato8 (Peptide 8) and its Prodrug Somato8-P (Peptide 8-P)

In an effort to develop an improved somatostatin analog, a cyclic N-methylated hexapeptide somatostatin analog denoted "Peptide 8" was selected from a combinatorial library of all possible N-methylated analogs of the potent hexa-cyclic somatostatin analog c(PFwKTF) (SEQ ID NO: 7) [31]. Out of the 30 analogs synthesized, only seven analogs were found to have somatostatin receptor (SSTR) affinity similar to that of the parent peptide, that is, selectivity towards SSTR2 and SSTR5 in the nanomolar range. From these seven analogs, one, named "Somato8" (previously "Peptide 8"), having the sequence c(PF(NMe)w(NMe)KT(NMe)F) (SEQ ID NO: 8), that contains three N-methylated amino acid residues, had the most promising PK parameters in vitro (including stability to intestinal enzymes and intestinal permeability). It was further investigated for its bioavailability following oral administration to rats compared to the parent sequence. The calculated absolute oral bioavailability of the multiple N-methylated analog in rats was ~10% which is nearly five times higher than the parent peptide [27].

Detailed Synthesis of Somato8

Peptide synthesis was carried out using CTC-resin (0.9 mmol/g) following standard Fmoc-strategy. Fmoc-Xaa-OH (1.2 eq.) were attached to the CTC-resin with N,N-diisopropylethylamin (DIEA; 2.5 eq.) in anhydrous dichloromethane (DCM, 0.8 mL/g resin) at room temperature (rt) for 1 h. The remaining trityl-chloride groups were capped by addition of a solution of MeOH (1 mL/g (resin)), DIEA (5:1; v:v) for 15 min. The resin was filtered and washed 5 times with DCM and 3 times with MeOH. The loading capacity was determined by weight after drying the resin under vacuum and ranged from 0.4-0.9 mmol/g.

On-resin Fmoc-Deprotection was performed by treating the Fmoc peptidyl-resin with 20% piperidine in NMP (v/v) for 10 minutes and a second treatment for 5 minutes. The resin was washed 5 times with NMP.

Standard Amino Acid Coupling was performed by adding a solution of Fmoc-Xaa-OH (2 eq.), O-(7-azabenzotriazole-1yl)-N,N,N',N'-tetramethyluronium-hexafluorophosphate (HATU) (2 eq.), 1-hydroxy-7-azabenzotriazole (HOAt; 2 eq.), and DIEA (3 eq.) in NMP (1 mL/g resin) to the free amino peptidyl-resin, shaking for 60 min at room temperature and washing 5 times with NMP.

For on-resin N-methylation, the linear Fmoc-deprotected peptide was washed with DCM (3×) incubated with a solution of 2-nitrobenzenesulfonylchloride (o-Ns-Cl, 4 eq.) and 2,4,6-Collidine (10 eq.) in DCM for 20 min at room temperature. The resin was washed with DCM (3×) and tetrahydrofuran (THF) abs. (5×). A solution containing PPh3 (5 eq.) and MeOH abs. (10 eq.) in THF abs. was added to the resin. Diisopropyl azodicarboxylate (DIAD, 5 eq.) in a small amount THF abs. is added stepwise to the resin and the solution was incubated for 15 min and washed with THF (5×) and NMP (5×). For o-Ns deprotection, the o-Ns-peptidyl-resin was stirred in a solution of mercaptoethanol (10 eq.) and 1,8-diazabicyclo[5.4.0]undec-7-ene (DBU, 5 eq.) in NMP (1 mL/g resin) for 5 minutes. The deprotection procedure was repeated once more and the resin was washed 5 times with NMP.

For complete cleavage from the resin the linear peptides were treated three times with a solution of DCM and hexafluoroisopropanol (HFIP; 4:1; v:v) at room temperature for half an hour and the solvent evaporated under reduced pressure.

To achieve cyclization, Diphenylphosphoryl Azide (DPPA, 3 eq.) was added to a solution of linear peptide in DMF (1 mM peptide concentration) and NaHCO$_3$ (5 eq.) at room temperature and the solution was stirred over night or until no linear peptide could be observed by HPLC-MS. The solvent was evaporated to a small volume under reduced pressure and the peptides precipitated in saturated NaCl solution and washed two times in HPLC grade water.

For removal of acid labile side chain protecting group, cyclized peptides were stirred in a solution of TFA, water and TIPS (95:2.5:2.5) at room temperature for one hour or until no more protected peptide could be observed by HPLC-MS and then precipitated in diethylether. The precipitated peptide was collected after centrifugation and decantation and then washed with diethylether and collected two more times.

Orthogonal reductive deprotection of the benzyl-group via hydrogenolysis was performed using a palladium catalyst on activated carbon (10% Pd/C with 50% H$_2$O as stabilizer, 15 mg/mmol) and hydrogen atmosphere (1 atm. H$_2$) at room temperature. The completion of the deprotection was monitored by HPLC-MS, the catalyst was removed over diatomaceous earth and the solvent was removed under pressure.

Synthesis of Somato8 Dihexyloxycarbonyl Prodrug "Somato8-P"

Somato8 was dissolved in acetonitrile and DIEA (3 eq.) was added. The solution was cooled in ice/water and under stirring hexyloxycarbonylchloride (Hoc-Cl, 3.1 eq.) was added dropwise. The solution was stirred in the cold for 1 hr. and at room temperature for three hours or until no free peptide could be observed by HPLC-MS. After reaction completion the solvent was evaporated and the product precipitated by hexane.

The structures of Somato8 (SEQ ID NO: 8) and its prodrug are illustrated in Scheme 2:

Scheme 2. Structures of Peptide 8 and its prodrug Peptide 8-P.

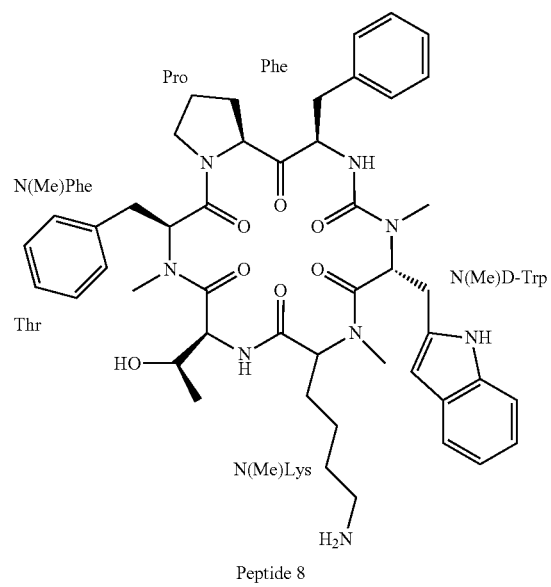

Peptide 8

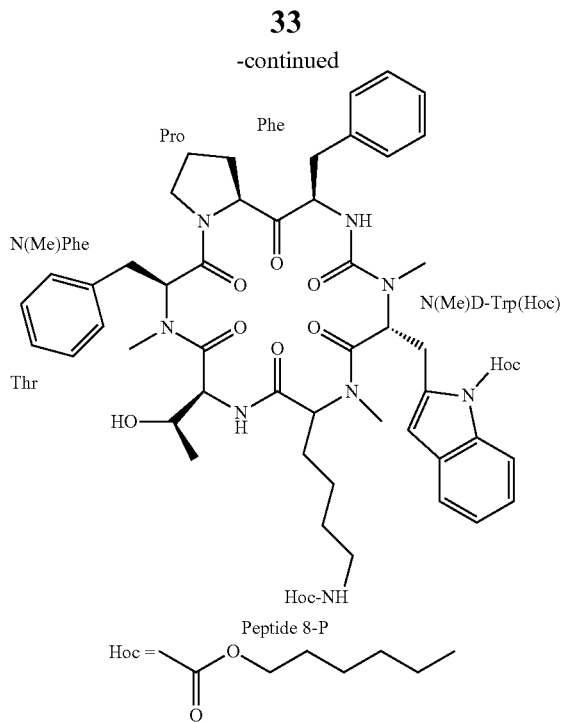

Peptide 8-P

Hoc =

Example 3. Backbone Cyclic Somatostatin Analogs and their Prodrugs

In an attempt to identify novel somatostatin analogs, libraries of backbone cyclic peptides have been previously prepared with compounds having identical or highly similar sequences to the somatostatin pharmacophoric sequences. Four libraries, each containing 96 compounds, were synthesized and screened for their binding affinities to somatostatin receptors. Following the screening process, several candidates were further investigated for their metabolic stability and pharmacodynamic profile compared to SRIF and to octreotide. Some of the compounds are PTR-3046 (SEQ ID NO: 9) [28], PTR-3205 (SEQ ID NO: 10) [29] and PTR-3173 (SEQ ID NO: 3) [30] depicted in Scheme 3:

Scheme 3: Structures of backbone cyclic analogs. A. PTR-3173, B. PTR-3046, C. PTR-3205.

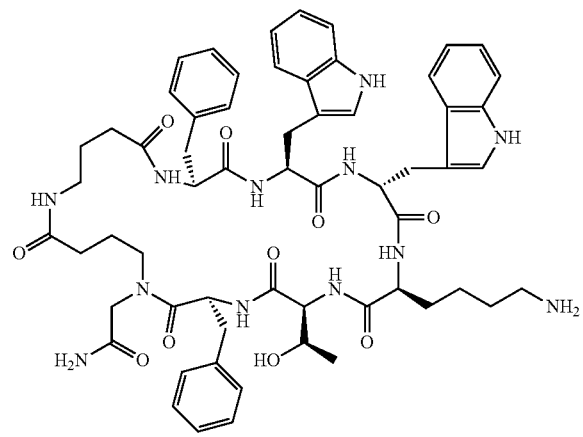

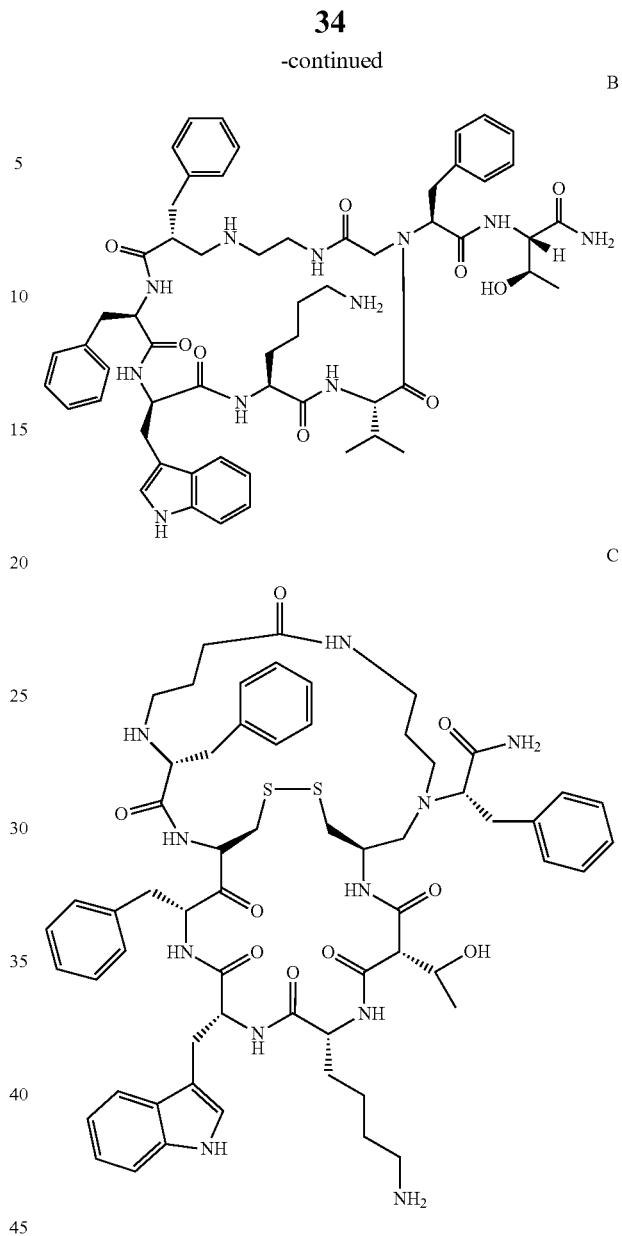

All backbone cyclic analogs were found to be stable against enzymatic degradation in serum and renal homogenate. However, their biological activity and selectivity varied toward the somatostatin receptors: while PTR-3046 was found to be selective toward the SSTR5 (IC50 in the nanomolar range), PTR-3205 was found to be selective towards SSTR2 and PTR-3173 was selective towards the SSTR2, SSTR4 and SSTR5. These analogs were also evaluated for their in vivo efficacy compared to octreotide. PTR-3173 was found to be 1000-fold more potent in the in vivo inhibition of GH than that of glucagon, with no effect on insulin secretion at physiological concentrations (GH: insulin potency ratio >10,000). This was the first description of a long-acting somatostatin analog possessing complete in vivo selectivity between GH and insulin inhibition. PTR-3046 inhibits bombesin- and caerulein-induced amylase and lipase release from the pancreas without inhibiting GH or glucagon release. PTR-3173 has been reported to bind uniquely to SSTR2, SSTR4 and SSTR5 in vitro with outstanding in vivo selectivity in GH inhibition [30]. All backbone cyclic analogs were found to be stable against enzymatic degradation in serum and renal homogenate.

The active N-methylated sequence (NMe)w-(NMe)K-T-(NMe)F-(SEQ ID NO: 11) was incorporated into the framework of the backbone cyclic analog PTR 3173 to form the somatostatin analog Somato3M (SEQ ID NO: 12), and its three hexyloxycbarbonyl prodrug, namely Somato3M-P (Scheme 4) was prepared in the same manner as Octreotide-P:

good prediction for in-vivo oral absorption of compounds [22]. The Caco-2 model is a widely used tool in the academia and pharmaceutical industry to evaluate and predict compounds' permeability mechanism. The Caco-2 system consists of human colon cancer cells that multiply and grow to create a monolayer that emulate the human small intestinal mucosa [23].

Scheme 4. Structure of A. Somato3M and B. its prodrug Somato3M-P.

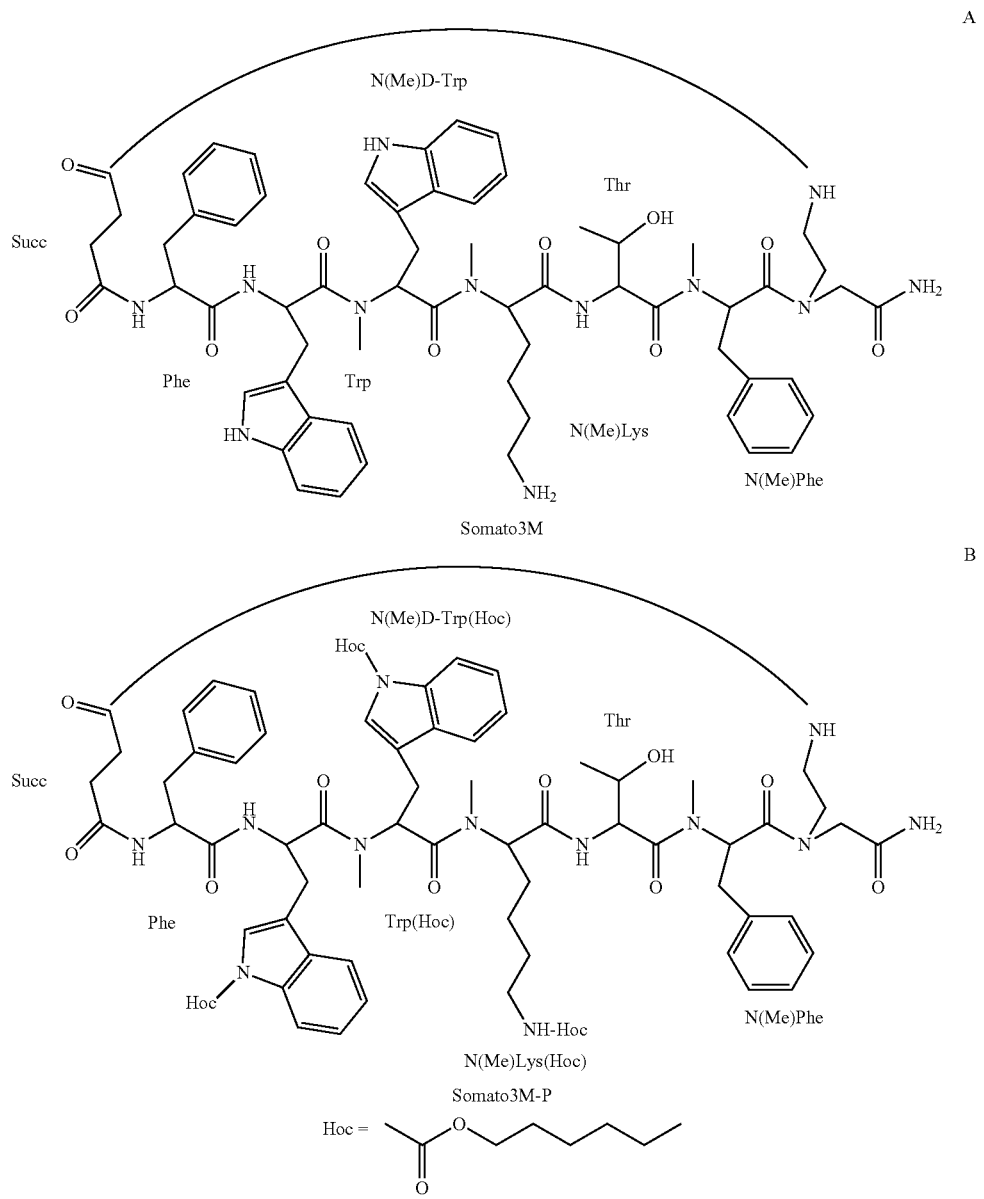

Each combination of bridge type and length imposes certain pharmacodynamics selectivity towards the somatostatin receptor subtypes. In addition, the N-methylation at different sites may elevate intestinal permeability.

Example 4. Intestinal Permeability and Oral Bioavailability Studies

In-vitro permeability studies model are essential for development of peptides as therapeutic agents, as they allow Transport studies were performed through the Caco-2 monolayer mounted in an Ussing-type chamber set-up with continuous trans-epithelial electrical resistance (TEER) measurements to assure TEER between 800 and 1200 $\Omega \ast cm^2$. HBSS supplemented with 10 mM IVIES and adjusted to pH 6.5 were used as transport medium in the donor compartment and pH 7.4 in the acceptor compartment. The donor solution contained the test compound. The effective permeability coefficients (Papp) were calculated from concentration-time profiles of each of the tested compounds in the acceptor chamber [24]. In every assay, the compounds were compared to the standards atenolol and metoprolol which represent para-cellular and trans-cellular permeability mechanisms respectably [25].

Permeability mechanism of compounds is studied by evaluating the Papp of a compound from the apical to the basolateral (A-to-B) membrane and its Papp from the basolateral to the apical membrane (B-to-A). The A-to-B assay simulates passive and transporter-mediated permeability. The B-to-A assay is essential complementary experiment indicative of the activity of P-gp. The ratio of the A-to-B and B-to A Papps (efflux ratio) is calculated to determine the permeability mechanism. A significant difference between the permeability coefficients in the two directions (efflux ratio of 1.5-2 or above), is a strong indication of active transport or efflux system involvement [26].

It is important to note that the involvement of efflux system is actual indication that the prodrug is permeate through the enterocytes membrane and afterwards removed from these cells by the efflux system. To further study the efflux system involved in the permeability mechanism, a Caco-2 study in the presence of verapamil (100 mM), a known P-gp inhibitor is performed.

Example 5: In Vitro Intestinal Permeability Studies with the Octreotide Prodrug (OCT-Hoc-2) in the Caco-2 Model Among the cell-based models, the most popular is the well-established Caco-2 cell culture model, originating from human colorectal adenocarcinoma cells. Caco-2 cells spontaneously differentiate into an epithelial monolayer similar in structure to that of the intestinal epithelium, including functional properties of mature enterocytes. These include formation of microvilli, tight-junctional complexes and expression of various transporters, efflux systems and brush-border enzymes. The cells are grown on semi-permeable membrane supports, which enhances their polarization and maximizes their similarity to the intestinal epithelial membrane while allowing transport studies across it.

Growth and Maintenance of the Cells

Caco-2 cells were obtained from ATCC (Manassas, Va., USA) and grown in 75 cm2 flasks with approximately 0.75×106 cells/flask at 37° C. in a 5% CO2 atmosphere and at a relative humidity of 95%. The culture growth medium consisted of Dulbecco's Modified Eagle Medium supplemented with 10% heat-inactivated fetal bovine serum, 1% nonessential amino acids, 2 mM sodium pyruvate, 2 mM Penicillin-Streptomycin solution and 2 mM L-glutamine. The medium was replaced three times weekly. For the transport studies, cells in a passage range of 53-60 were seeded at a density of 25×105 cells/cm2 on pretreated culture inserts of a polycarbonate membrane with 0.4 µm pores and a surface area of 1.1 cm2 and then placed in 12-well transwell plates, 12 mm, Costar™. The culture medium was changed every other day. Transport studies were performed 21-22 days after seeding, allowing the cells proper proliferation, differentiation and development of their proper morphology.

Experimental Protocol

Transport studies (apical to basolateral, A to B) were initiated by removing the medium from both sides of the monolayer and replacing it with 600 µL of apical buffer (0.025M D-glucose monohydrate, 0.02M MES biological Buffer, 1.25 mM calcium chloride and 0.5 mM magnesium chloride in Hanks Balanced Salt Solution, filtered and titrated to pH 6.5 with NaOH) and 1500 µL of basolateral buffer (0.025M D-glucose monohydrate, 0.02M HEPES biological Buffer, 1.25 mM calcium chloride, and 0.5 mM magnesium chloride in Hanks Balanced Salt Solution, filtered and titrated to pH 7.4 with NaOH), both preheated to 37° C. The cells were incubated for 30 min at 37° C. with shaking (100 cycles/min). After the incubation period, the buffers were removed and replaced with 1500 µL of basolateral buffer on the basolateral side. Test solutions containing tested drug or prodrug (10 µg/mL) in apical buffer were preheated to 37° C. and added (600 µL) to the apical side of the monolayer. Samples (50 µL) were immediately taken from the apical side at the beginning of the experiment, leaving a 550 µL apical volume during the experiment. For the period of the experiment, the cells were kept at 37° C. with shaking. At predetermined times (20, 40, 60, 80, 100, 120 and 150 min), 200 µL samples were taken from the basolateral side and replaced with the same volume of fresh basolateral buffer to maintain a constant volume and sink conditions. For the basolateral to apical study (B to A), the test solution of the drug or prodrug was placed in the basolateral chamber, followed by immediate sampling from the basolateral side and continued sampling from the apical side at predetermined times, similarly to the A-to B protocol. Samples were kept frozen at a temperature of −20° C. pending analysis by HPLC-MS.

During the three-week period of differentiation of the cells, the transepithelial electrical resistance (TEER) of the cells was measured continuously using the Millicell2 ERS Epithelial Volt-Ohm meter and STX01 electrode (Millipore corporation, Billerica, Mass.), to evaluate the proper development of the monolayer. For Caco-2 cells, at 21-22 days post seeding, the cells reach their full differentiation and generation of the monolayer, reaching stable TEER values of 300-500 $\Omega \times cm^2$. Inserts with deviational values were not used.

Atenolol, a commonly used marker for paracellular permeability in Caco-2 cells, was used in combination with metoprolol, a commonly used marker for transcellular permeability.

Similarly, to the A-to-B studies of the peptide permeability, 600 µl of apical buffer containing 10 µg/ml of atenolol and metoprolol each were added to the apical side of the monolayer and a sample (50 µl) was immediately withdrawn from the apical side. Further samples of 200 µl were taken at predetermined times up to 150 min, and similar volumes of blank buffer were added to the basolateral side to maintain constant volume and sink conditions during the experiment. The samples were analyzed for atenolol and metoprolol content by means of HPLC-MS, followed by calculation of atenolol and metoprolol Papp.

Data Analysis

The samples obtained from the Caco-2 permeability experiments were analyzed for peptide, atenolol and metoprolol content using the HPLC-MS system. The permeability coefficient (Papp) of each peptide was calculated from the linear plot of drug accumulated vs. time, using the following equation: Papp=dQ/dt C0×A where dQ/dt is steady state appearance rate of the drug on the receiver side, C0 is the initial concentration of the drug on the donor side, and A is the exposed tissue surface area, 1.1 cm2 in the specified experiments.

As can be seen in FIG. 1, the octreotide prodrug OCT-Hoc-2 permeate in the A to B direction through enterocyte monolayer, with permeability coefficient values less than atenolol (0.03 cm/s×$10^6$), the marker for paracellular permeability.

It is known that the intestinal absorption of Octreotide is poor. As previously shown in Caco2 studies, the mechanism of absorption of octreotide is via the paracellular pathway and the formulative efforts to elevate its permeability had only minor success. The octreotide prodrug of the present invention is the first one that demonstrated enhanced intestinal permeability via the transcellular pathway.

The permeability mechanism of the pro-drug was also studied by evaluating the $P_{app}$ of the compounds from the basolateral to the apical membrane (BA). The $P_{app}$ BA of the Octreotide prodrug (11.95 cm/s×10$^6$) were significantly higher than the $P_{app}$ AB(0.03 cm/s×10$^6$)(P<0.05, indicating efflux system involvement. The use of specific delivery systems and/or absorption enhancers designed for inhibiting p-gp activity is therefore preferred. Such delivery system is for example, an advanced lipid based Self-Emulsifying Drug Delivery System termed Advanced Pro-NanoLiposphere (PNL) pre-concentrate.

Example 6: Metabolic Stability Studies

Generally, the purpose of metabolic stability studies is to evaluate the compounds rate of elimination in the presence of hostile environments: a rat plasma or extractions of the gut wall. In these environments, compounds are prone to enzymatic degradation, as there are high concentrations of peptidases, esterases, lipases and other peptides that metabolize xenobiotics to building units for synthesizing essential structures in the body [27, 28].

Specifically, in our case, the purposes of the metabolic stability studies are (1) to prove that the prodrug is digested by esterases to furnish the drug and (2) to demonstrate that the somatostatin peptides and their prodrugs are stable to digestion in the intestine.

The enzymatic reactions are performed as follows: 2 mM stock solutions of the tested compounds are diluted with serum or purified brush border membrane vesicles (BBMVs) solution to a final concentration of 0.5 mM. During incubation at 37° C. samples are taken for a period of 90 minutes. The enzymatic reaction is stopped by adding 1:1 v/v of ice cold acetonitrile and centrifuge (4000 g, 10 min) before analysis. Preparation of BBMVs: The BBMVs is prepared from combined duodenum, jejunum, and upper ileum (male Wistar rats) by a Ca++ precipitation method. Purification of the BBMVs is assayed using GGT, LAP and alkaline phosphatase as membrane enzyme markers The peptides and prodrugs are subjected to rat plasma and followed their degradation. Rat plasma is known to be rich with esterases. Next, peptides and prodrugs are subjected to extractions of the gut wall (brush border membrane vesicles, BBMV) and followed their rate of degradation. The BBMV assay determines the peptides stability in the presence of digestive enzymes in the brush border membrane of the intestine especially peptidases.

Selected peptides and prodrugs are subjected to additional in vitro assay to evaluate the involvement of liver metabolism, through the Pooled Human Liver Microsome assay. Liver microsomes are subcellular particles derived from the endoplasmic reticulum of hepatic cells. These microsomes are a rich source of drug metabolizing enzymes, including cytochrome P-450. Microsome pools from various sources are useful in the study of xenobiotic metabolism and drug interactions.

Example 7: Pharmacokinetic Study

The pharmacokinetic in-vivo study allows a further evaluation of the prodrug concept in the whole animal. The PK studies are performed for example in conscious Wistar male rats. An indwelling cannula is implanted in the jugular vein 24 hours before the PK experiment to allow full recovery of the animals from the surgical procedure. Animals (n=4) receive either an IV bolus dose or oral dose of the investigated compound. Blood samples (with heparin, 15 U/ml) are collected at several time points for up to 6 hours post administration and are assayed by HPLC-MS method. Non-compartmental pharmacokinetic analysis is performed using WinNonlin software.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

REFERENCES

1. Ovadia O, Greenberg S, Laufer B, Gilon C, Hoffman A, Kessler H. Improvement of drug-like properties of peptides: the somatostatin paradigm. Expert Opin. Drug Discov. Informa UK Ltd London, UK; 2010; 5:655-71.
2. Grozinsky-Glasberg S, Shimon I, Korbonits M, Grossman A B. Somatostatin analogues in the control of neuroendocrine tumours: efficacy and mechanisms. Endocr. Relat. Cancer. BioScientifica; 2008; 15:701-20.
3. Patel Y C, Murthy K K, Escher E E, Banville D, Spiess J, Srikant C B. Mechanism of Action of Somatostatin: An Overview of Receptor Function and Studies of the Molecular Characterization and Purification of Somatostatin Receptor Proteins Model of Somatostatin Action.
4. Lahlou H, Guillermet J, Hortala M, Vernejoul F, Pyronnet S, Bousquet C, et al. Molecular Signaling of Somatostatin Receptors. Ann. N. Y. Acad. Sci. Blackwell Publishing Ltd; 2004; 1014:121-31.
5. Reichlin S. Somatostatin. N. Engl. J. Med. 1983; 309: 1495-501.
6. Mezey É, Hunyady B, Mitra S, Hayes E, Liu Q, Schaeffer J, et al. Cell Specific Expression of the SST2A and SST5 Somatostatin Receptors in the Rat Anterior Pituitary. Endocrinology. Oxford University Press; 1998; 139:414-9.
7. Kumar U, Sasi R, Suresh S, Patel A, Thangaraju M, Metrakos P, et al. Subtype-selective expression of the five somatostatin receptors (hSSTR1-5) in human pancreatic islet cells: a quantitative double-label immunohistochemical analysis. Diabetes. 1999; 48.
8. Mitra S W, Mezey É, Hunyady B, Chamberlain L, Hayes E, Foor F, et al. Colocalization of Somatostatin Receptor sst5 and Insulin in Rat Pancreatic β-Cells[1]. Endocrinology. 1999; 140:3790-6.
9. Schally A V. Oncological applications of somatostatin analogues. Cancer Res. American Association for Cancer Research Inc.; 1988; 48:6977-85.
10. Scarpignato C, Pelosini I. Somatostatin analogs for cancer treatment and diagnosis: an overview. Chemotherapy. 2001; 47 Suppl 2:1-29.
11. Pollak M N, Schally A V. Mechanisms of Antineoplastic Action of Somatostatin Analogs. Exp. Biol. Med. SAGE PublicationsSage U K: London, England; 1998; 217:143-52.
12. Bousquet C, Puente E, Buscail L, Vaysse N, Susini C. Antiproliferative effect of somatostatin and analogs. Chemotherapy. Karger Publishers; 2001; 47 Suppl 2:30-9.

13. Oberg K. Future aspects of somatostatin-receptor-mediated therapy. Neuroendocrinology. Karger Publishers; 2004; 80 Suppl 1:57-61.
14. Heron I, Thomas F, Dero M, Gancel A, Ruiz J M, Schatz B, et al. Pharmacokinetics and efficacy of a long-acting formulation of the new somatostatin analog BIM 23014 in patients with acromegaly. J. Clin. Endocrinol. Metab. 1993; 76:721-7.
15. Hruby V, Balse P. Conformational and Topographical Considerations in Designing Agonist Peptidomimetics from Peptide Leads. Curr. Med. Chem. 2000; 7:945-70.
16. Weide T, Modlinger A, Kessler H. Spatial Screening for the Identification of the Bioactive Conformation of Integrin Ligands. doi.org. Springer Berlin Heidelberg; 2006; 1-50.
17. Lamberts S W J, van der Lely A-J, de Herder W W, Hofland L J. Octreotide. Wood A J J, editor. N. Engl. J. Med. Massachusetts Medical Society; 1996; 334:246-54.
18. Bauer W, Briner U, Doepfner W, Haller R, Huguenin R, Marbach P, et al. SMS 201-995: a very potent and selective octapeptide analogue of somatostatin with prolonged action. Life Sci. 1982; 31:1133-40.
19. Gilon C, Halle D, Chorev M, Selincer Z, Byk G. Backbone cyclization: A new method for conferring conformational constraint on peptides. Biopolymers. Wiley Subscription Services, Inc., A Wiley Company; 1991; 31:745-50.
20. Assaf Friedler ‡ Nehama Zakai §, Orit Karni §, Yehoshua C. Broder §, Lea Baraz I, Moshe Kotler I, et al. Backbone Cyclic Peptide, Which Mimics the Nuclear Localization Signal of Human Immunodeficiency Virus Type 1 Matrix Protein, Inhibits Nuclear Import and Virus Production in Nondividing Cells†. American Chemical Society; 1998;
21. Ovadia O, Linde Y, Haskell-Luevano C, Dirain M L, Sheynis T, Jelinek R, et al. The effect of backbone cyclization on PK/PD properties of bioactive peptide-peptoid hybrids: the melanocortin agonist paradigm. Bioorg. Med. Chem. 2010; 18:580-9.
22. Chatterjee J, Gilon C, Hoffman A, Kessler H. N-Methylation of Peptides: A New Perspective in Medicinal Chemistry. Acc. Chem. Res. 2008; 41:1331-42.
23. Linde Y, Ovadia O, Safrai E, Xiang Z, Portillo F P, Shalev D E, et al. Structure-activity relationship and metabolic stability studies of backbone cyclization and N-methylation of melanocortin peptides. Biopolymers. NIH Public Access; 2008; 90:671-82.
24. Han H K, Amidon G L. Targeted prodrug design to optimize drug delivery. AAPS PharmSci. Springer; 2000; 2:E6.
25. Jornada D, dos Santos Fernandes G, Chiba D, de Melo T, dos Santos J, Chung M. The Prodrug Approach: A Successful Tool for Improving Drug Solubility. Molecules. Multidisciplinary Digital Publishing Institute; 2015; 21:42.
26. Simplicio A L, Clancy J M, Gilmer J F. Prodrugs for Amines. Molecules. Molecular Diversity Preservation International; 2008; 13:519-47.
27. Biron E, Chatterjee J, Ovadia O, Langenegger D, Brueggen J, Hoyer D, et al. Improving Oral Bioavailability of Peptides by Multiple N-Methylation: Somatostatin Analogues**.
28. Chaim Gilon ‡, Martin Huenges §, Barbara Mathä §, Gary Gellerman ⊥, Vered Hornik ⊥, Michel Afargan ⊥, et al. A Backbone-Cyclic, Receptor 5-Selective Somatostatin Analogue: Synthesis, Bioactivity, and Nuclear Magnetic Resonance Conformational Analysis†. American Chemical Society; 1998;
29. Falb E, Salitra Y, Yechezkel T, Bracha M, Litman P, Olender R, et al. A bicyclic and hsst2 selective somatostatin analogue: design, synthesis, conformational analysis and binding. Bioorg. Med. Chem. 2001; 9:3255-64.
30. Afargan M, Janson E T, Gelerman G, Rosenfeld R, Ziv O, Karpov O, et al. Novel Long-Acting Somatostatin Analog with Endocrine Selectivity: Potent Suppression of Growth Hormone But Not of Insulin. Endocrinology. 2001; 142:477-86.
31. Veber D F, Freidlinger R M, Perlow D S, et al. Nature 1981; 292(5818):55-8,
32. Cherniakov, Domb A J, Hoffman A. Self-nano-emulsifying drug delivery systems: an update of the biopharmaceutical aspects. Expert Opin Drug Deliv. 2015 July; 12(7):1121-33.
33. Klinger et al., Enhancing oral bioavailability of cyclic RGD hexa-peptides by the lipophilic prodrug charge masking approach: redirection of peptide intestinal permeability from paracrine to transcellular pathway.

The invention claimed is:

1. A somatostatin prodrug comprising a lipophilic carbamate derivative of a somatostatin peptide or peptide analog, wherein the lipophilic carbamate is having a formula selected from the group consisting of:

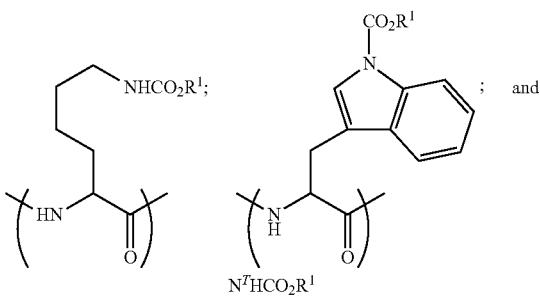

wherein $R^1$ is a primary alkyl having the formula $n-C_nH_{2n+1}$, wherein n is in the range of 3 to 15.

2. The somatostatin prodrug of claim 1, wherein the carbamate moiety is formula

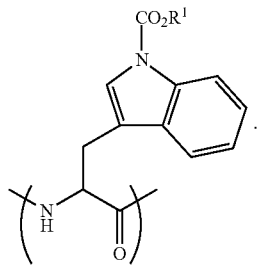

3. The somatostatin prodrug of claim 1, wherein $R^1$ is n-hexyl.

4. The somatostatin prodrug of claim 1, wherein at least one positively charged group of the somatostatin amino acid sequence is masked with a lipophilic carbamate moiety in the lipophilic carbamate somatostatin derivative.

5. The somatostatin prodrug of claim 1, wherein the somatostatin peptide or peptide analog comprises at least one N-methylated amino acid residue.

6. The somatostatin prodrug of claim 1, wherein the somatostatin peptide or peptide analog comprises 5-15 amino acid residues.

7. The somatostatin prodrug of claim 1, wherein the somatostatin peptide or peptide analog is cyclic.

8. The somatostatin prodrug of claim 1, wherein the somatostatin peptide or peptide analog is selected from the group consisting of octreotide (SEQ ID NO: 1), somatuline (lanreotide, SEQ ID NO: 2), PTR-3173 (Somatoprim, SEQ ID NO: 3), and Pasireotide (SEQ ID NO: 4).

9. The somatostatin prodrug of claim 1, wherein the somatostatin peptide or peptide analog comprises a sequence selected from SEQ ID NO: 5 and SEQ ID NO: 6.

10. The somatostatin prodrug of claim 8, wherein the somatostatin peptide or peptide analog is octreotide (SEQ ID NO: 1) coupled with at least one oxycarbonyl moiety.

11. The somatostatin prodrug of claim 10, comprising octreotide coupled to three hexyloxycarbonyl moieties, wherein the somatostatin prodrug has the structure:

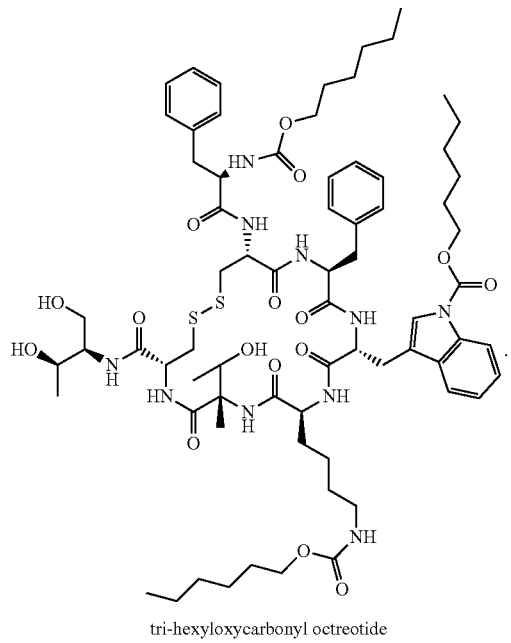 [SMILES: CCCCCCOC(=O)NCCCC[C@@H]1NC(=O)[C@@H](Cc2cn(C(=O)OCCCCCC)c3ccccc23)NC(=O)[C@H](Cc2ccccc2)NC(=O)[C@@H](NC(=O)[C@@H](Cc2ccccc2)NC(=O)OCCCCCC)CSSC[C@@H](C(=O)N[C@H](CO)[C@@H](C)O)NC(=O)[C@](C)(C(C)O)NC1=O]

tri-hexyloxycarbonyl octreotide

12. The somatostatin prodrug of claim 1, wherein the somatostatin analog is a head-to-tail cyclic N-methylated hexapeptide having the sequence c(PF(NMe)w(NMe)KT(NMe)F), wherein (NMe)w is N-methyl D-Tryptophan and (NMe)F is N-methyl-Phenylalanine (peptide 8, SEQ ID NO: 8).

13. The somatostatin prodrug of claim 1, comprising two hexyloxycarbonyl moieties coupled to peptide 8 (SEQ ID NO: 8) to form the structure:

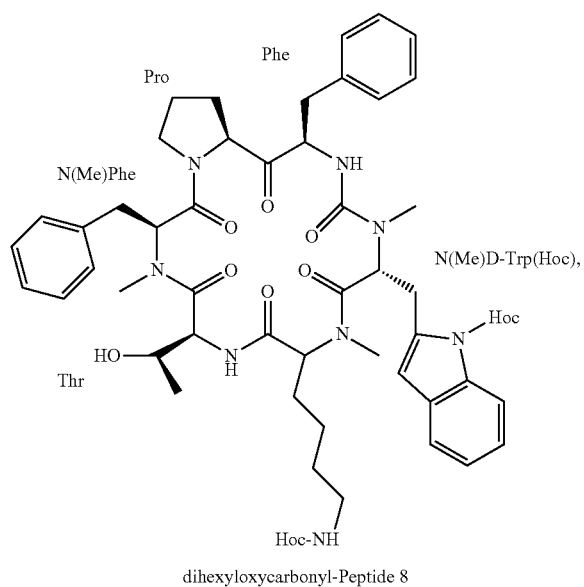

dihexyloxycarbonyl-Peptide 8 wherein Hoc represents hexyloxycarbonyl.

14. The somatostatin prodrug of claim 1, wherein the somatostatin analog is a backbone cyclic somatostatin analog, wherein the backbone cyclized somatostatin analog is selected from the group consisting of: PTR 3173 (SEQ ID NO: 3), PTR 3046 (SEQ ID NO: 9), PTR 3205 (SEQ ID NO: 10), PTR 3171 (SEQ ID NO: 13), PTR 3113 (SEQ ID NO: 14), PTR 3123 (SEQ ID NO: 15), PTR 3209 (SEQ ID NO: 16), PTR 3183 (SEQ ID NO: 17), PTR 3185 (SEQ ID NO: 18), PTR 3201 (SEQ ID NO: 19), PTR 3203 (SEQ ID NO: 20), PTR 3197 (SEQ ID NO: 21), PTR 3207 (SEQ ID NO: 22), and PTR 3229 (SEQ ID NO: 23).

15. The somatostatin prodrug of claim 14, comprising three hexyloxycarbonyl moieties coupled to the backbone cyclic peptide Phe-Trp-(NMe)DTrp-(NMe)Lys-Thr-(NMe)Phe to form the formula:

16. A pharmaceutical composition comprising as an active ingredient a somatostatin prodrug according to claim 1 and a pharmaceutically acceptable carrier, excipient, or diluent.

17. A method of treating a disease or disorder associated with somatostatin expression or activity, comprising administering to a subject in need thereof, a pharmaceutical composition according to claim 16.

18. The method of claim 17, wherein the disease or disorder is selected from the group consisting of metabolic disease or disorder, endocrine disease or disorder, cancer and angiogenesis.

19. A method of increasing the permeability and bioavailability of a somatostatin peptide or peptide analog, comprising masking at least one terminal amine or side-chain nitrogen atom of the somatostatin peptide or analog to form a lipophilic carbamate somatostatin prodrug, wherein the lipophilic carbamate is having a formula selected from the group consisting of:

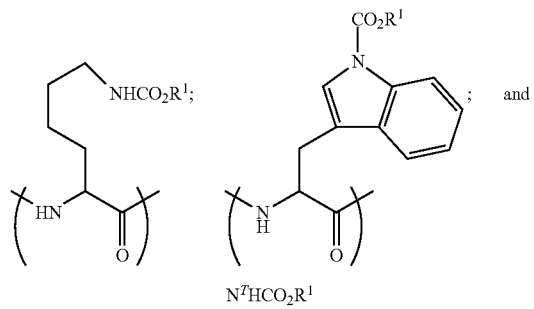

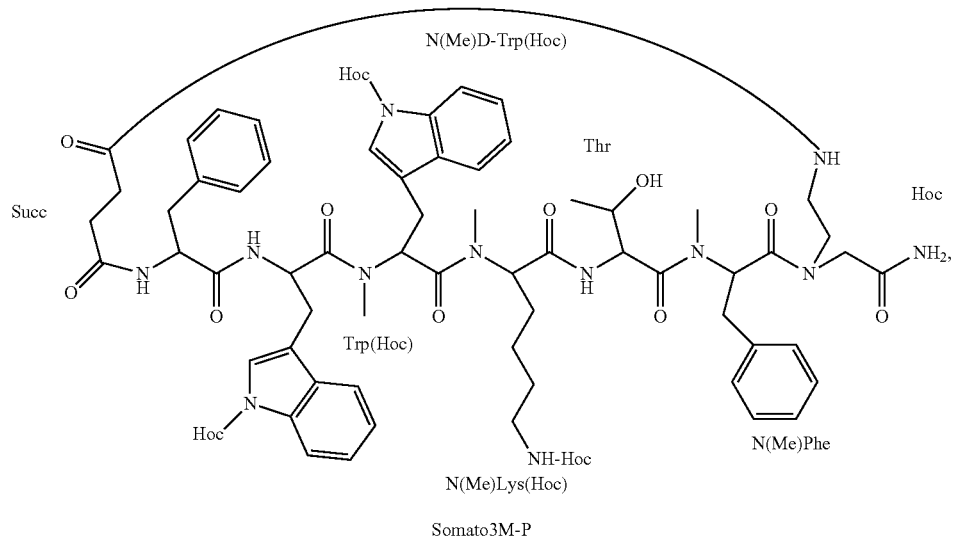

Somato3M-P wherein Hoc represents hexyloxycarbonyl.

wherein $R^1$ is a primary alkyl having the formula n-$C_nH_{2n+1}$ wherein n is in the range of 3 to 15.

* * * * *